(12) United States Patent
Halter et al.

(10) Patent No.: US 12,089,964 B2
(45) Date of Patent: Sep. 17, 2024

(54) MICROCONTROLLER FOR RECORDING AND STORING PHYSIOLOGICAL DATA

(71) Applicant: THE TRUSTEES OF DARTMOUTH COLLEGE, Hanover, NH (US)

(72) Inventors: Ryan Halter, Lyme, NH (US); Gunnar C. Pope, Lebanon, NH (US)

(73) Assignee: THE TRUSTEES OF DARTMOUTH COLLEGE

( * ) Notice: Subject to any disclaimer, the term of this patent is extended or adjusted under 35 U.S.C. 154(b) by 811 days.

(21) Appl. No.: 17/270,971

(22) PCT Filed: Aug. 23, 2019

(86) PCT No.: PCT/US2019/047950
§ 371 (c)(1),
(2) Date: Feb. 24, 2021

(87) PCT Pub. No.: WO2020/041730
PCT Pub. Date: Feb. 27, 2020

(65) Prior Publication Data
US 2021/0251574 A1    Aug. 19, 2021

Related U.S. Application Data

(60) Provisional application No. 62/722,520, filed on Aug. 24, 2018.

(51) Int. Cl.
*A61B 5/00* (2006.01)
*A61B 5/08* (2006.01)
(Continued)

(52) U.S. Cl.
CPC .............. *A61B 5/7232* (2013.01); *A61B 5/08* (2013.01); *A61B 5/369* (2021.01); *A61B 5/389* (2021.01);
(Continued)

(58) Field of Classification Search
CPC ........ A61B 5/726; A61B 5/7232; A61B 5/369; A61B 5/389; A61B 5/7225; A61B 5/681;
(Continued)

(56) References Cited

U.S. PATENT DOCUMENTS 6,009,385 A    12/1999  Summerfield
6,069,976 A    5/2000   Kim
(Continued)

OTHER PUBLICATIONS

International Patent Application No. PCT/US2019/047950, International Search Report and Written Opinion dated Nov. 4, 2019, 21 pgs.

*Primary Examiner* — Vincent F Boccio
(74) *Attorney, Agent, or Firm* — Cozen O'Connor

(57) ABSTRACT

A microcontroller for recording and storing physiological data includes an analog-to-digital converter for converting analog physiological sensor signals to digital signals, a sample buffer for holding a temporal sequence of the digital signals, a central processing unit (CPU), and a non-volatile memory. The non-volatile memory includes (i) a code storage encoding machine-readable data compression instructions that, when executed by the CPU, control the CPU to (a) transform the temporal sequence of the digital signals to produce transformed physiological data characterized by a set of transformation coefficients and (b) compress the set of transformation coefficients to generate compressed physiological data, and (ii) a data storage configured to contain several different instances of the compressed physiological data respectively associated with several different instances of the temporal sequence of the digital signals.

21 Claims, 16 Drawing Sheets

(51) Int. Cl.
*A61B 5/369* (2021.01)
*A61B 5/389* (2021.01)
*H03M 7/30* (2006.01)
*A61B 5/0531* (2021.01)

(52) U.S. Cl.
CPC ............ *A61B 5/681* (2013.01); *A61B 5/7225* (2013.01); *A61B 5/726* (2013.01); *H03M 7/3082* (2013.01); *A61B 5/0531* (2013.01)

(58) Field of Classification Search
CPC ......... A61B 5/7235; A61B 5/08; A61B 5/024; A61B 5/0531; H03M 7/3082; H03M 7/30
USPC ........................................................ 707/693
See application file for complete search history.

(56) References Cited

U.S. PATENT DOCUMENTS

| | | | |
|---|---|---|---|
| 6,556,941 | B2 | 4/2003 | Mallory et al. |
| 6,577,770 | B1 | 6/2003 | Martin et al. |
| 6,774,822 | B1 | 8/2004 | Thomson |
| 7,020,701 | B1 | 3/2006 | Gelvin et al. |
| 7,196,641 | B2 * | 3/2007 | Huang ................. G10L 19/008 704/E19.044 |
| 7,672,834 | B2 | 3/2010 | Smaragdis |
| 7,995,124 | B2 | 8/2011 | Dai |
| 9,135,113 | B2 | 9/2015 | Ojalvo et al. |
| 9,472,033 | B2 | 10/2016 | Agrafioti et al. |
| 2002/0041658 | A1 | 4/2002 | Henderson et al. |
| 2008/0287748 | A1 * | 11/2008 | Sapounas ............. A61B 5/6833 600/300 |
| 2011/0010405 | A1 * | 1/2011 | Gupta .................. G06F 17/148 708/203 |
| 2012/0123232 | A1 * | 5/2012 | Najarian .................. G16Z 99/00 600/407 |
| 2014/0093881 | A1 * | 4/2014 | Sugnet ..................... H03M 7/30 435/6.12 |
| 2015/0335292 | A1 | 11/2015 | Mittal |
| 2016/0044439 | A1 * | 2/2016 | Mittal ..................... H04W 4/70 370/311 |
| 2016/0314055 | A1 | 10/2016 | Bagchi et al. |

* cited by examiner

| Bit | | | | | | | | | | | | | | | |
|---|---|---|---|---|---|---|---|---|---|---|---|---|---|---|---|
| 15 | 14 | 13 | 12 | 11 | 10 | 9 | 8 | 7 | 6 | 5 | 4 | 3 | 2 | 1 | 0 |
| | | | | | $A_4[0]$ | | | | | | | $D[0].addr[0]$ | | | |
| | | | | | $A_4[1]$ | | | | | | | $D[0].addr[1]$ | | | |
| | | | | | $A_4[2]$ | | | | | | | $D[1].addr[0]$ | | | |
| | | | | | $A_4[3]$ | | | | | | | $D[1].addr[1]$ | | | |
| | | | | | ... | | | | | | | ... | | | |
| | | | | | $A_4[10]$ | | | | | | | $D[5].addr[0]$ | | | |
| | | | | | $A_4[11]$ | | | | | | | $D[5].addr[1]$ | | | |
| | | | | $D[1]$ | | | | | | $D[0]$ | | | | | |
| | | | | $D[3]$ | | | | | | $D[2]$ | | | | | |
| | | | | $D[5]$ | | | | | | $D[4]$ | | | | | |
| | | | | $D[x]$ | | | | $D[x].addr[1]$ | | | | $D[x].addr[0]$ | | | |
| | | | | ⋮ | | | | ⋮ | | | | ⋮ | | | |

MICROCONTROLLER FOR RECORDING AND STORING PHYSIOLOGICAL DATA

CROSS-REFERENCE TO RELATED APPLICATIONS

The present application is a 35 U.S.C. § 371 filing of International Application No. PCT/US2019/047950 filed Aug. 23, 2019, which claims priority to U.S. Provisional Patent Application Ser. No. 62/722,520 filed Aug. 24, 2018, which is incorporated herein by reference in its entirety.

GOVERNMENT SUPPORT

This invention was made with government support under grant numbers CNS1314281 and CNS1619970 awarded by the National Science Foundation. The government has certain rights in the invention.

BACKGROUND

Advances in miniaturizing and increasing computational functionality of wearable biosensors have revolutionized the delivery of modern healthcare services by providing pragmatic and timely solutions that are scalable outside of the hospital. Embedded microcontrollers are used in some wearable biosensor systems, providing high-performance digital signal processing capabilities at ultra-low power consumption due to efficient usage of their single core central processing units. The gains in power efficiency and compact size come at the cost of low internal storage capabilities (typically in the ~1 KB to 512 KB range) and lower processing capabilities when compared to larger, multi-core microprocessors and system-on-a-chip solutions.

Designers of wearable, ultra-low-power or energy harvesting biosensors must address the challenge of maximizing sensor performance while minimizing physical size, weight, and power consumption to create unobtrusive wearable biosensors. High-quality recording of physiological signals is commonly associated with high data rates and large storage requirements for embedded systems, often requiring the use of external memory devices, such as microSD cards, peripheral memory chips (EEPROM, Flash, etc.), or wireless transmission to a phone or other off-system device.

Electrodermal activity (EDA) is a physiological phenomenon that refers to electrical variations occurring on the surface of the skin due to changes in sweat secretion. The electrodermal response is exclusively activated by the sympathetic nervous system, making it a leading biosignal to monitor psychological or physiological arousal of the autonomic nervous system. Because of this relationship, EDA monitoring has been used for multiple applications including evaluating anxiety and stress, detecting the orienting response, providing biofeedback for epilepsy mitigation, recognizing emotional states, and many more. Some applications rely on acute, short-term EDA changes to impact the user (e.g., identification of epileptic events), while, in others, long-term trending is more important (e.g., long-term anxiety and stress monitoring.)

Measures associated with EDA are typically grouped into two classes of tonic and phasic features. Tonic EDA measures relate to the slowly varying skin conductance level. Tonic features include the average skin conductance level, the standard deviation of the EDA signal, the signal maximum amplitude, and the signal minimum amplitude. Phasic features relate to the rapid fluctuations of skin conductance in response to a stimulus and have been helpful in evaluating stress, anxiety, the orienting response, and applications related to emotional sensing.

In the general field of physiological sensing, various methods for compressing physiological signals have been developed over the past twenty years to improve sensor size and power. Data compression methods can often be separated into lossless or lossy compression. Lossless compression methods create perfect reconstructions from compressed data but are often processing intensive and challenging to implement on resource-constrained devices. In contrast, lossy compression methods create reconstructions which are approximations to the original data and enable large levels of data compression at the expense of signal distortion.

SUMMARY

In an embodiment, a microcontroller for recording and storing physiological data includes an ADC for converting analog physiological sensor signals to digital signals, a sample buffer for holding a temporal sequence of the digital signals, a central processing unit (CPU), and a non-volatile memory. The non-volatile memory includes (i) a code storage encoding machine-readable data compression instructions that, when executed by the CPU, control the CPU to (a) transform the temporal sequence of the digital signals to produce transformed physiological data characterized by a set of transformation coefficients and (b) compress the set of transformation coefficients to generate compressed physiological data, and (ii) a data storage configured to contain several different instances of the compressed physiological data respectively associated with several different instances of the temporal sequence of the digital signals.

In an embodiment, a method for recording and storing physiological data, includes, within a microcontroller, performing steps of (a) sampling, over time and via an analog-to-digital converter, an analog physiological sensor signal received by the microcontroller to produce a temporal sequence of digital signals, (b) transforming the temporal sequence of the digital signals to produce transformed physiological data characterized by a set of transformation coefficients, (c) compressing the set of transformation coefficients to generate compressed physiological data, and (d) encoding the compressed physiological data in a non-volatile memory onboard the microcontroller.

DETAILED DESCRIPTION OF EXAMPLE EMBODIMENTS

Figure 1:
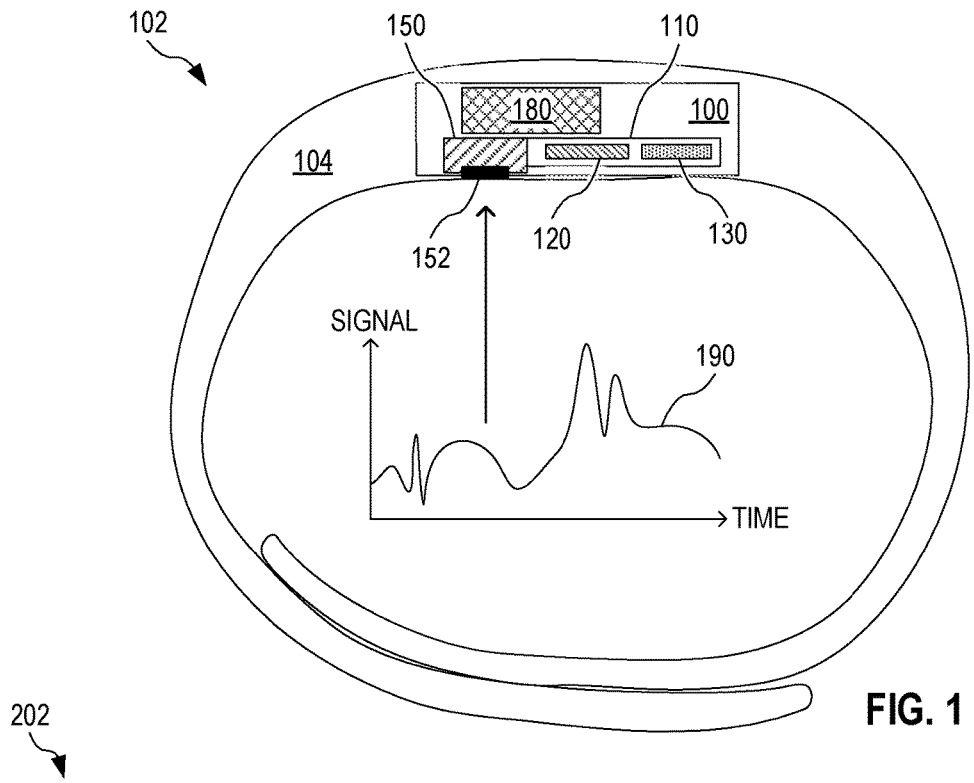
FIG. 1 illustrates, in an example use scenario, a microcontroller for recording and storing physiological data, according to an embodiment.

FIG. 1 illustrates, in an example use scenario, one microcontroller 110 for recording and storing physiological data. Microcontroller 110 is communicatively coupled with a sensor 150. Sensor 150 senses a physiological signal 190 through an interface 152. Microcontroller 110 and sensor 150 are implemented in a device 100. Device 100 further includes a power source 180 that supplies power to sensor 150 and microcontroller 110. Power source 180 is, for example, a battery, an energy harvesting unit, or a combination of a battery and an energy harvesting unit.

Microcontroller 110 includes a data compression module 120 and a data storage 130. Data compression module 120 compresses physiological data obtained from sensor 150. The resulting compressed physiological data is stored in data storage 130. Data compression module 120 allows microcontroller 110 to record physiological signal 190 over a long period of time without relying on an external memory, or wireless connection to an external storage device, for storage of the recorded physiological data.

Sensor 150 may be electrodermal activity (EDA) sensor, a temperature sensor (e.g., for measuring body temperature), a heart rate variability sensor, a surface electromyography sensor (e.g., for measuring muscle activity), an electroencephalography sensor (e.g., for measuring brain activity), a photoplethysmogram sensor (e.g., for measuring pulse and/or blood oxygenation level), or another sensor sampling physiological signals at a bandwidth similar to these sensors. In one implementation, interface 152 is electrical. For example, when sensor 150 is an EDA sensor, interface 152 may include two electrodes for measuring the conductivity at the skin of a user. An electroencephalography sensor embodiment of sensor 150 or a surface electromyography sensor embodiment of sensor 150 is also configured with electrodes in interface 152. In another implementation, for example when sensor 150 is a photoplethysmogram sensor, interface 152 is optical. In this implementation, interface 152 may include a photodetector for sensing a light level from a user, and interface 152 may further include a light source for illuminating the user. Embodiments of sensor 150 configured to sense heart rate variability or a temperature may utilize either one of an electrical and optical interface 152.

Physiological signal 190 may be periodic or, as shown in FIG. 1, aperiodic. Aperiodic signals present particular challenges for data compression. Certain embodiments of data compression module 120 are configured to apply a lossy data compression scheme that compresses an aperiodic signal in a manner that, despite the data compression scheme being lossy, allows for later reconstruction of the original physiological signal 190 to a high approximation.

By virtue of using microcontroller 110, as opposed to systems with multi-core microprocessors or system-on-a-chip solutions and as opposed to systems with a large onboard data storage or systems relying on wireless communication with an external storage device, device 100 has relatively low power requirements and may be implemented as a relatively small package.

In the example use scenario depicted in FIG. 1, device 100 is embedded in a wristband 104 to form a wearable physiological sensing device 102. It is understood that the use of device 100 is not limited to implementation in a wrist band, and that device 100 may be implemented in other types of wearable devices or even in non-wearable devices that may benefit from the low power requirements, small form factor, and onboard storage capabilities of microcontroller 110. It is further understood that microcontroller 110 may be provided as a standalone device for integration with a third-party sensor 150.

Removing the external storage requirements of a physiological sensing device has many system-level implications when designing wearable biosensors. Sensor size and costs are reduced by eliminating external memory chips, wireless communication ICs, and radio antennas. Reduced power requirements lead to smaller battery sizes. Smaller batteries improve wearability and comfort of a wearable biosensor. Therefore, microcontroller 110 and device 100 offer clear improvements in size, comfort, and cost. These low-resource design strategies utilized in microcontroller 110 and device 100 could be useful in remote monitoring applications (in-home care, primary care, workplace mHealth, etc.) where long-term monitoring is desirable, but wireless connectivity is limited and/or unavailable. Microcontroller 110 and device 100 could be useful in extreme mobile environments, such as military applications or competitive athletics, where sensor weight and form factor have high premiums. Device 100 could additionally be integrated with a wireless transmitter to allow for low-power data storage within the microcontroller 110 during periods without wireless connectivity and permit wireless data transmission only at the most opportune times.

Figure 2:
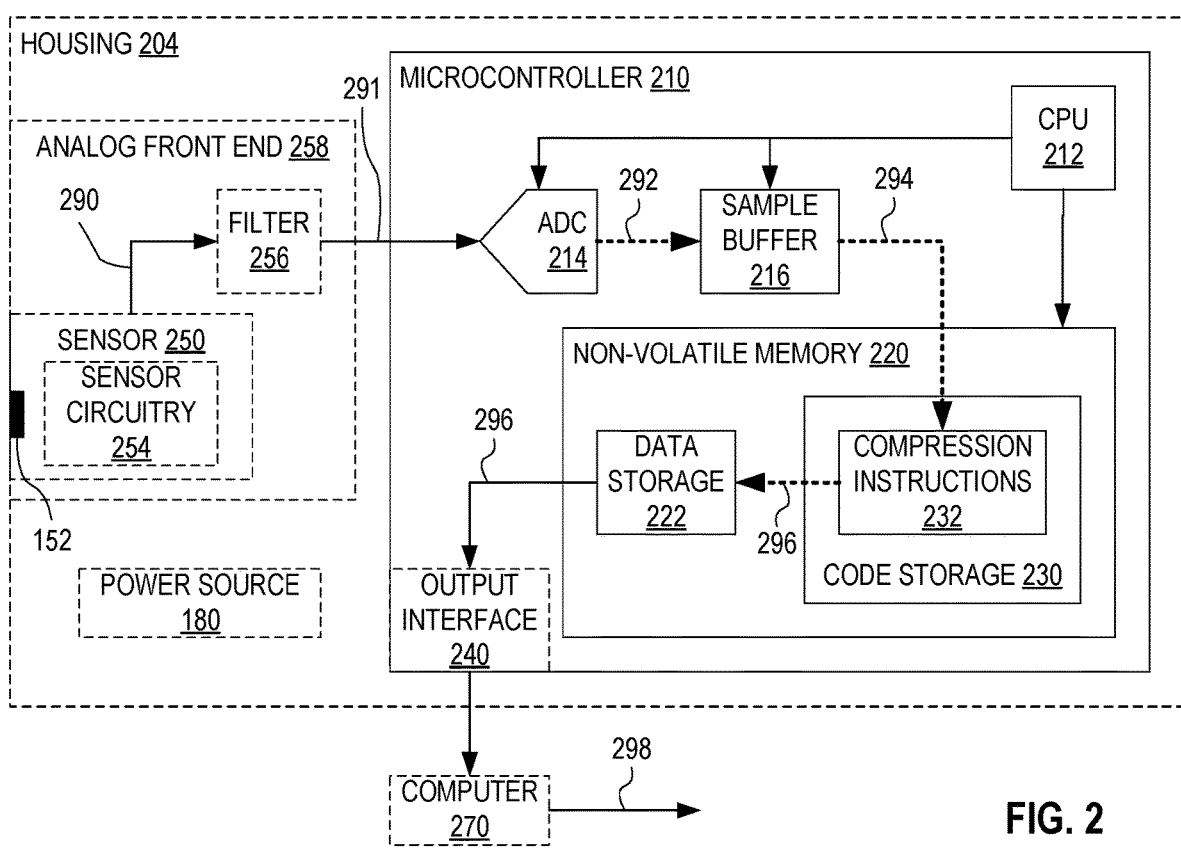
FIG. 2 illustrates a microcontroller having non-volatile memory containing a data storage and machine-readable data compression instructions, according to an embodiment.

FIG. 2 illustrates one microcontroller 210 having non-volatile memory 220 containing a data storage 222 and machine-readable data compression instructions 232. Microcontroller 210 is an embodiment of microcontroller 110. Microcontroller 210 includes a central processing unit (CPU) 212, an analog-to-digital converter (ADC) 214, a sample buffer 216, and a non-volatile memory 220. Data storage 222 is an embodiment of data storage 130. CPU 212 and data compression instructions 232 cooperate to form an embodiment of data compression module 120.

Memory 220 is, for example, flash memory or ferroelectric random-access memory (FRAM). FRAM holds certain advantages, such as lower power usage, as compared to flash memory. FRAM is therefore advantageous over flash memory when microcontroller 210 is subject to power constraints, such as when microcontroller 210 is implemented in device 100 and intended to operate over a long period of time powered only by a small battery and/or an energy harvesting unit (embodiments of power source 180). Since memory 220 is non-volatile, microcontroller 210 may enter an off-state or a low-power, e.g., a sleep mode or deep sleep mode, without loss of the information stored in memory 220, thereby further enhancing the power efficiency of microcontroller 210.

CPU 212 is communicatively coupled with ADC 214, sample buffer 216, and memory 220, for example via a communication bus not shown in FIG. 2. CPU 212 may be a single-core CPU. Sample buffer 216 may be implemented as random-access memory (RAM) or non-volatile memory. Although shown in FIG. 2 as being external to non-volatile memory 220, sample buffer 216 may, without departing from the scope hereof, instead be part of memory 220.

Memory 220 includes a data storage 222 and a code storage 230. Code storage 230 includes machine-readable data compression instructions 232. In operation, microcontroller 210 samples, via ADC 214, an input signal 291. Input signal 291 is an analog physiological sensor signal received, directly or indirectly, from a sensor 250. Sensor 250 is an embodiment of sensor 150 and includes interface 152.

ADC 214 converts each sample of input signal 291 to a digital signal 292. Microcontroller 210 stores a plurality of digital signal 292, obtained over time via ADC 214, to sample buffer 216 as a temporal sequence 294 of digital signals 292. CPU 212 executes data compression instructions 232 that control CPU 212 to compress temporal sequence 294, thereby generating compressed physiological data 296. Microcontroller 210 stores compressed physiological data 296 to data storage 222. Microcontroller 210 may repeat this process with several sampling periods of input signal 190 to compress several corresponding instances of temporal sequence 294 and store the corresponding instances of compressed physiological data 296 to data storage 222 until it is possible or convenient to communicate these instances of compressed physiological data 296 to an external system. Microcontroller 210 may include an output interface 240, such as a serial interface, through which microcontroller 210 may output compressed physiological data 296, stored in data storage 222, to an external computer 270.

In one scenario, a user wears wearable physiological sensing device 102, implementing microcontroller 210 and sensor 250 for an extended time period, such as several hours, a day, or several days. During this extended time period, microcontroller samples input signal 190, through several sampling periods, and stores a series of corresponding instances of compressed physiological data 296 to data storage. At a later time, for example at the end of the extended time period, a user connects output interface 240 to external computer 270 (e.g., a laptop or a smartphone) and downloads all stored instances of compressed physiological data 296 from data storage 222 to external computer 270. External computer 270 may be equipped with software that decompresses each instance of compressed physiological data 296 to reconstruct the corresponding instances of temporal sequence 294, so as to generate reconstructed physiological signals 298. This reconstruction may be exact or approximate. In one implementation, data compression instructions 232 encode a lossy compression algorithm such that the reconstruction is not exact. However, in this implementation, data compression instructions 232 may be configured to minimize deviations between reconstructed physiological signals 298 and digital signals 292 for properties of the physiological data deemed most interesting.

Sensor 250 may include sensor circuitry 254 that processes signals received from interface 152. Sensor circuitry 254 may include an amplifier that amplifies a signal from interface 152. In one embodiment, sensor circuitry 254 includes a transducer that converts a signal, received via interface 152, from one form to another. For example, sensor circuitry 254 may include a photodiode that converts a light input to a voltage output, wherein the value of the voltage output corresponds to the intensity of the light input. Sensor 250 may include an auditory, visual, or haptic feedback element that can be used to communicate with a user when certain physiological events have occurred or an intervention is needed.

Microcontroller 210 may be coupled with sensor 250 in a device 202. Device 202 may include a housing 204. Housing 204 may be configured to be wearable, such that device 202 forms an embodiment of device 102. Housing 204 is, for example, wristband 104. However, without departing from the scope hereof, device 202 may be a package suitable for implementation in a third-party system, which may or may not be wearable. For example, device 202 may include a printed circuit board containing microcontroller 210 and sensor 250, wherein the printed circuit board has a receptacle for a battery. Interface 152 may include connections extending away from the printed circuit board. In another example, microcontroller 210 and sensor 250 are implemented on two different printed circuit boards.

In certain embodiments, device 202 includes an analog front end 258 that contains sensor 250 and at least one filter 256. Filter 256 filters an analog physiological sensor signal 290 outputted by sensor 250, to generate input signal 291 as a filtered version of analog physiological sensor signal 290. Filter 256 may be a frequency filter that selects a certain spectral range of analog physiological sensor signal 290. In one embodiment, filter 256 is a low-pass filter that removes spectral components of analog physiological sensor signal 290 above a cutoff frequency. This low-pass filter may suppress noise in analog physiological sensor signal 290. For applications where the physiologically interesting property of analog physiological sensor signal 290 varies only relatively slowly, such as in EDA sensing, the cut-off frequency may be one hertz or less. In applications where the physiologically interesting property of analog physiological sensor signal 290 contains a periodic component, filter 256 may be a bandpass filter with a bandpass that spans an expected range of the frequency of the periodic component, or filter 256 may be a low-pass filter with a cutoff frequency that exceeds the expected range of the frequency of the periodic component by at least a small margin. In one implementation, filter 256 is configured to be anti-aliasing at the sampling rate used by microcontroller 210. For example, microcontroller 210 may be operating at a sample rate in the range between 1.5 and 10 hertz, while filter 256 is an anti-aliasing low-pass bandpass filter with a cut-off frequency of 1.0 hertz or less. Generally, filter 256 may reduce the complexity of analog physiological sensor signal 290 and, as a result, focus the information content of temporal sequence 294 to improve the performance of the data compression algorithm encoded in data compression instructions 232.

In one embodiment, microcontroller 210 is characterized by a current draw no greater than 10 milliamperes and a clock rate no greater than 32 megahertz. In this embodiment, memory 220 may have capacity no greater than 1 megabyte (even if including sample buffer 216), and CPU 212 may be configured to process word lengths of no more than 24 bits. In another embodiment, microcontroller 210 is characterized by a current draw no greater than 0.1 milliamperes and a clock rate no greater than 16 megahertz or no greater than 1 megahertz. In this embodiment, memory 220 may have capacity no greater than 64 kilobytes (even if including sample buffer 216), and CPU 212 may be configured to process word lengths of no more than 16 bits. The bit depth of ADC 214 is, for example, in the range from 10 to 16 bits or in the range from 10 to 12 bits.

The dashed arrows in FIG. 2 indicate a process flow. It is understood that (a) in most physical implementations of microcontroller 210, signals and data flow along one or more communication busses as commanded by CPU 212 and (b) signals and data do not flow into or out of data compression instructions 232. Rather, CPU 212 executes data compression instructions 232 on temporal sequence 294 to generate compressed physiological data 296. During this execution, temporal sequence 294 and compressed physiological data 296 may exist in a combination of one or more of sample buffer 216, data storage 222, another portion of memory 220, CPU 212, a RAM optionally included in microcontroller 210, and one or more communication busses.

Figure 3:
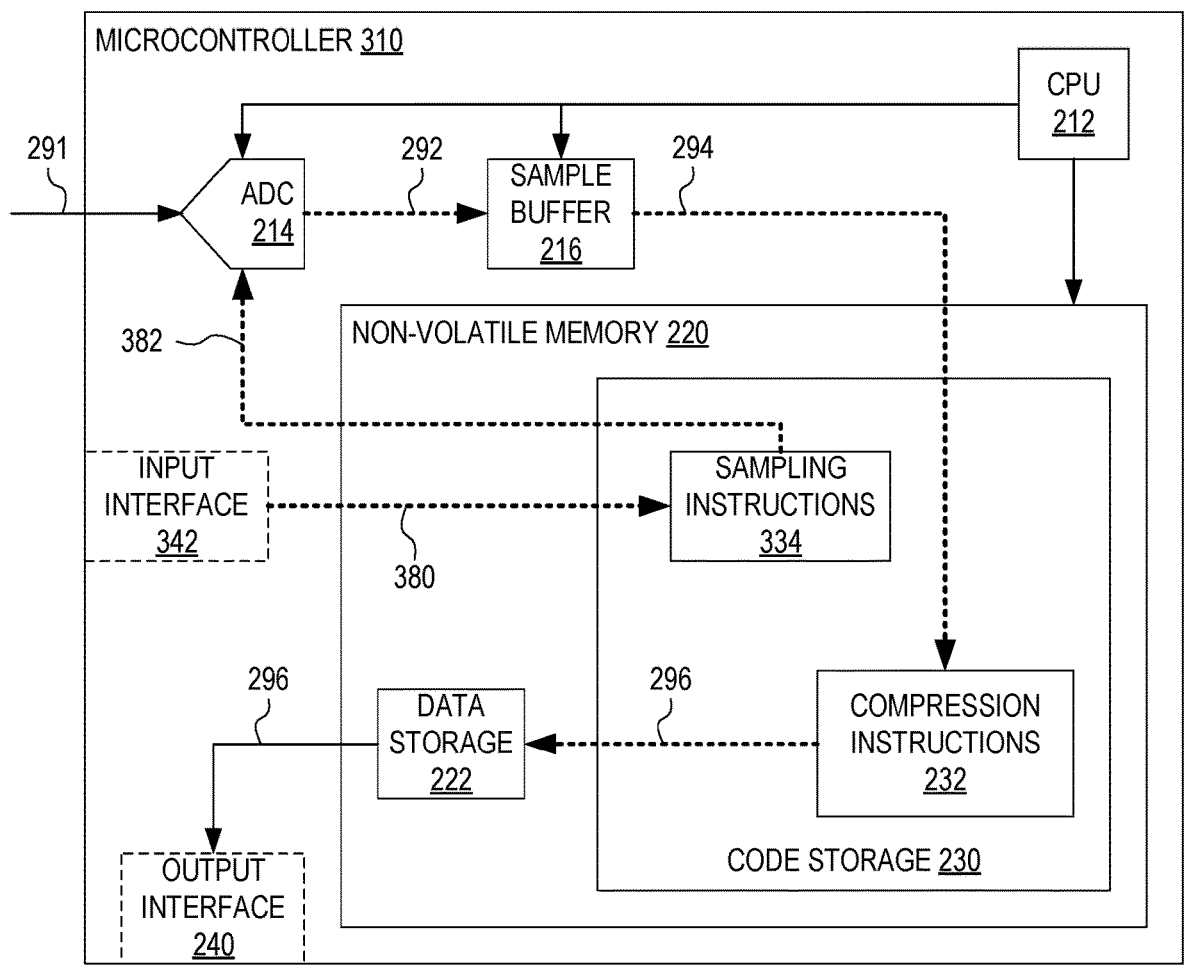
FIG. 3 illustrates a microcontroller having non-volatile memory containing data storage and both machine-readable data compression instructions and machine-readable sampling instructions, according to an embodiment.

FIG. 3 illustrates one microcontroller 310 having non-volatile memory 220 containing data storage 222 and both machine-readable data compression instructions 232 and machine-readable sampling instructions 334. Microcontroller 310 is an embodiment of microcontroller 210, wherein code storage 230 includes sampling instructions 334. When executed by CPU 212, sampling instructions 334 control CPU 212 to sample, via ADC 214 and over time, input signal 291 to obtain analog physiological sensor signals. Sampling instructions 334 may include a sampling rate at which each temporal sequence 294 is obtained. Sampling instructions 334 may further include a schedule specifying how often or when CPU 212 should obtain each instance of temporal sequence 294. In one example, this schedule specifies one or both of the frequency of successive samplings to obtain corresponding successive instances of temporal sequence 294, and a total number of instances of temporal sequence 294. Sampling instructions 334 may further include the number of digital signals 292 to be included in each temporal sequence 294.

In certain embodiments, each of sampling instructions 334 and data compression instructions 232 are interrupt-based. In such embodiments, microcontroller 310 may be configured to default to a low-power state. Sampling instructions 334 and data compression instructions 232 may then prompt microcontroller 310 to wake up from this low-power state to respectively sample input signal 291 and compress temporal sequence 294. The interrupt-based nature of sampling instructions 334 and data compression instructions 232 helps preserve power consumption by microcontroller 310 by maximizing time in the low-power state.

In one scenario, microcontroller 310 is woken up from a deep-sleep mode by sampling instructions 334. During execution of sampling instructions 334 to obtain one temporal sequence 294, microcontroller 310 returns to a sleep mode between each individual sampling of input signal 291. After completion of execution of data compression instructions 232, microcontroller 310 returns to the deep-sleep mode until woken up, according to sampling instructions 334, to obtain the next temporal sequence 294.

Microcontroller 310 may include an input interface 342 configured to accept a user specification 380 of one or more properties of the schedule of sampling instructions 334. User specification 380 may include one or more of a sampling rate, a schedule specifying the frequency of successive samplings to obtain corresponding successive instances of temporal sequence 294, a total number of instances of temporal sequence 294 to be obtained, and a number of digital signals 292 in each temporal sequence 294.

It is understood that other machine-readable instructions encoded in code storage 230 (not shown in FIG. 3) and/or a user input via input interface 342 may wake up microcontroller 310 from its low power state.

Figure 4:
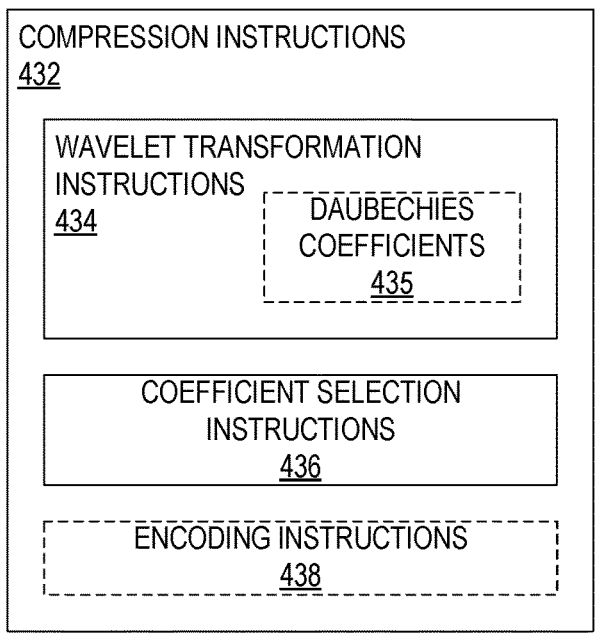
FIG. 4 illustrates a set of machine-readable data compression instructions based upon wavelet transformation of temporal sequence, according to an embodiment.

FIG. 4 illustrates one set of machine-readable data compression instructions 432 based upon wavelet transformation of temporal sequence 294. Data compression instructions 432 are an embodiment of data compression instructions 232. Data compression instructions 432 include wavelet transformation instructions 434 and coefficient selection instructions 436. Upon execution by CPU 212, wavelet transformation instructions 434 control CPU 212 to apply a discrete wavelet transformation (DWT) to temporal sequence 294 to generate transformed physiological data characterized by a set of transformation coefficients. The DWT may be a single-level DWT or a multi-level DWT. Upon execution by CPU 212, coefficient selection instructions 436 control CPU 212 to compress the set of transformation coefficients by selecting a subset of transformation coefficients to be retained as compressed physiological data 296.

Data compression instructions 432 may further include encoding instructions 438 that, upon execution by CPU 212, control CPU 212 to encode the selected transformation coefficients in data storage 222. Encoding instructions 438 may be configured to pack the selected transformation coefficients in data storage 222 in a manner that efficiently utilizes the word length of data storage 222. For example, when the word length of data storage 222 exceeds the bit depth of the selected transformation coefficients, encoding instructions 438 may be configured to encode data from two different transformation coefficients into one word in data storage 222. Encoding instructions 438 may also be configured to split the bits of one transformation coefficient between two or more different words in data storage 222.

In one embodiment, wavelet transformation instructions 434 are configured to utilize the Daubechies wavelet family. In this embodiment, wavelet transformation instructions 434 include a set of Daubechies scaling and wavelet coefficients 435.

In an alternative embodiment, not shown in FIG. 4, wavelet transformation instructions 434 are replaced by non-wavelet transformation instructions configured to apply a non-wavelet transformation, such as a Fourier transformation, a discrete cosine transformation, or a polynomial transformation. Fourier transformation and discrete cosine transformation may be particularly suitable for scenarios where the physiologically interesting property of input signal 291 is periodic in nature. It is understood that, in such scenarios, the period may vary over time. Since DWT is able to capture and localize temporal variations of a signal at a variety of scales, DWT is particularly advantageous when input signal 291 is aperiodic (see, for example, physiological signal 190 of FIG. 1).

Figure 5:
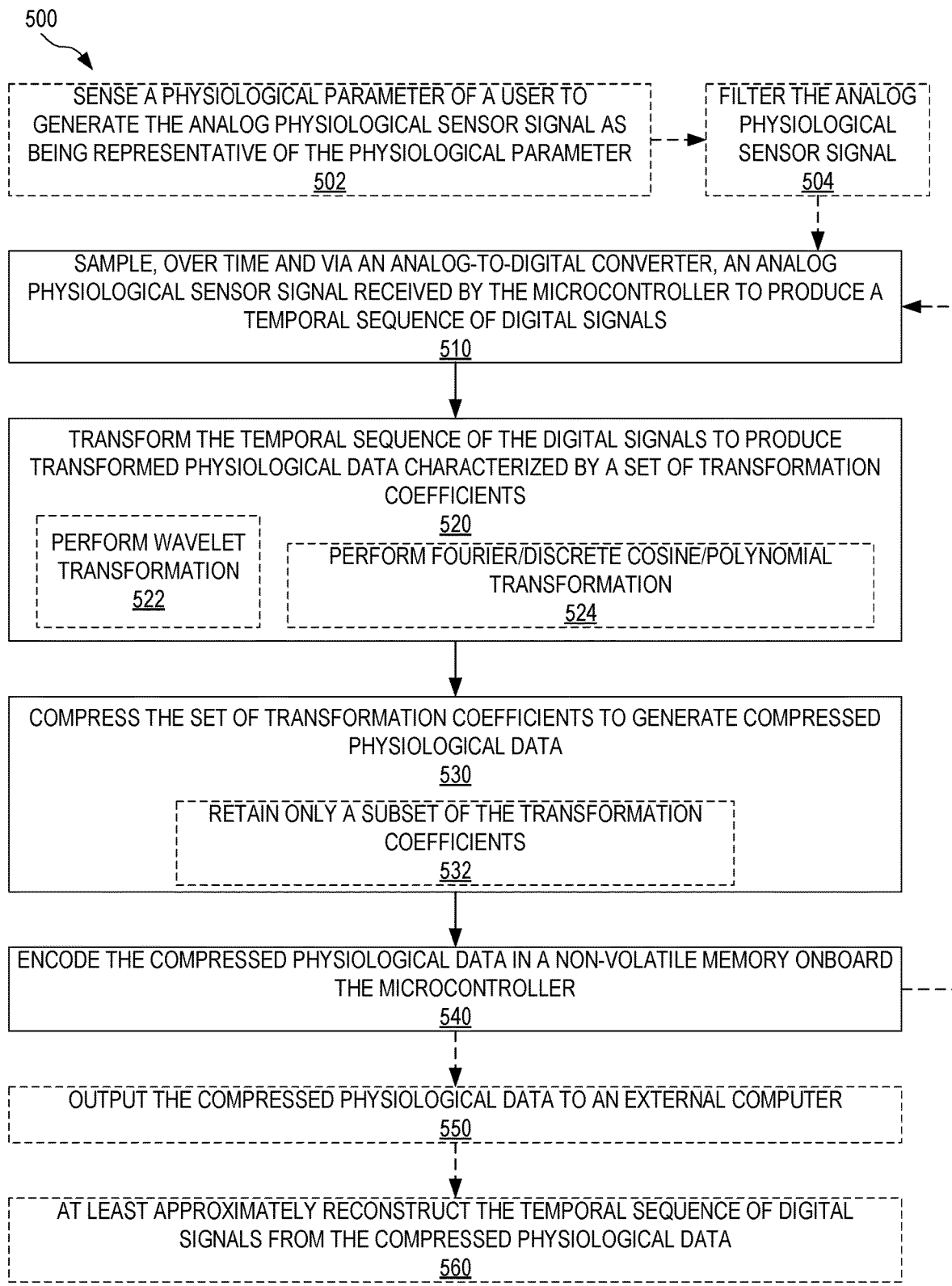
FIG. 5 illustrates a method for recording and storing physiological data, according to an embodiment.

FIG. 5 illustrates one method 500 for recording and storing physiological data. Method 500 is configured to compress the recorded physiological data and is therefore suitable for implementation in a wearable physiological sensing device, such as device 102, or in another device having only limited data storage capability. Method 500 includes steps 510, 520, 530, and 540, which are performed by a microcontroller, such as any of microcontrollers 110, 210, and 310.

Step 510 samples, over time and via an ADC, an analog physiological sensor signal received by the microcontroller. Step 510 thereby produces a temporal sequence of digital signals. In one example of step 510, microcontroller 310, upon execution of sample instructions 334 by CPU 212, samples input signal 291, over time, to produce temporal sequence 294, as discussed above in reference to FIG. 3. In this example, each digital signal 292 of temporal sequence 294 is stored to sample buffer 216.

Step 520 transforms the temporal sequence of the digital signals to produce transformed physiological data characterized by a set of transformation coefficients. Step 530 compresses the set of transformation coefficients to generate compressed physiological data. In one example of steps 520 and 530, microcontroller 310, upon execution of data compression instructions 232 by CPU 212, (a) transforms (in step 520) temporal sequence 294 to produce a set of transformation coefficients, and then (b) selects (in step 530) a subset of the transformation coefficients to compose compressed physiological data 296.

In an embodiment, step 530 includes a step 532 of retaining only a subset of the transformation coefficients. For example, step 532 may compress at least a portion of the transformation coefficients and retain, from this portion, only a set of transformation coefficients having magnitude exceeding the magnitude of all non-retained transformation coefficients of this portion.

Step 520 may include step 522 or step 524. Step 522 performs a wavelet transformation, e.g., a DWT. In one example of step 522, CPU 212 executes wavelet transformation instructions 434, as discussed above in reference to FIG. 4. Step 524 performs a non-wavelet transformation, such as a Fourier transformation, a discrete cosine transformation, or a polynomial transformation, as discussed above in reference to FIG. 4.

Step 540 encodes the compressed physiological data, i.e., the subset of transformation coefficients selected and retained in step 530, in a non-volatile memory onboard the microcontroller. In one example of step 540, CPU 212 executes encoding instructions 438, as discussed above in reference to FIG. 4.

Method 500 may further include a step 550 of outputting the compressed physiological data to an external computer. In one example of step 550, microcontroller 210 outputs compressed physiological data 296 to external computer 270 via output interface 240.

Embodiments of method 500 that include step 550 may further include a step 560. Step 560 is performed by the external computer and reconstructs, at least approximately, the temporal sequence of digital signals from the compressed physiological data outputted to the external computer in step 560. In one example of step 560, external computer 270 reconstructs, exactly or approximately, temporal sequence 294 from compressed physiological data 296, as discussed above in reference to FIG. 2.

Certain embodiments of method 500 further include a step 520, and optionally also a step 504. Step 502 senses a physiological parameter of a user to generate the analog physiological sensor signal as a representation of the physiological parameter. As discussed above in reference to FIG. 1, the physiological parameter may be EDA, respiration, heart rate variability, body temperature, brain activity, or muscle activity. In one example of step 502, sensor 250 senses a physiological parameter of a user to generate analog physiological sensor signal 290, as discussed above in reference to FIG. 2. Further, in this example as pertaining to embodiments of method 500 that do not include step 504, sensor 250 outputs analog physiological sensor signal 290 as input signal 291. Step 504 filters the analog physiological sensor signal. In one example of step 504, filter 256 filters analog physiological sensor signal 290 to produce input signal 291, as discussed above in reference to FIG. 2.

Figure 6:
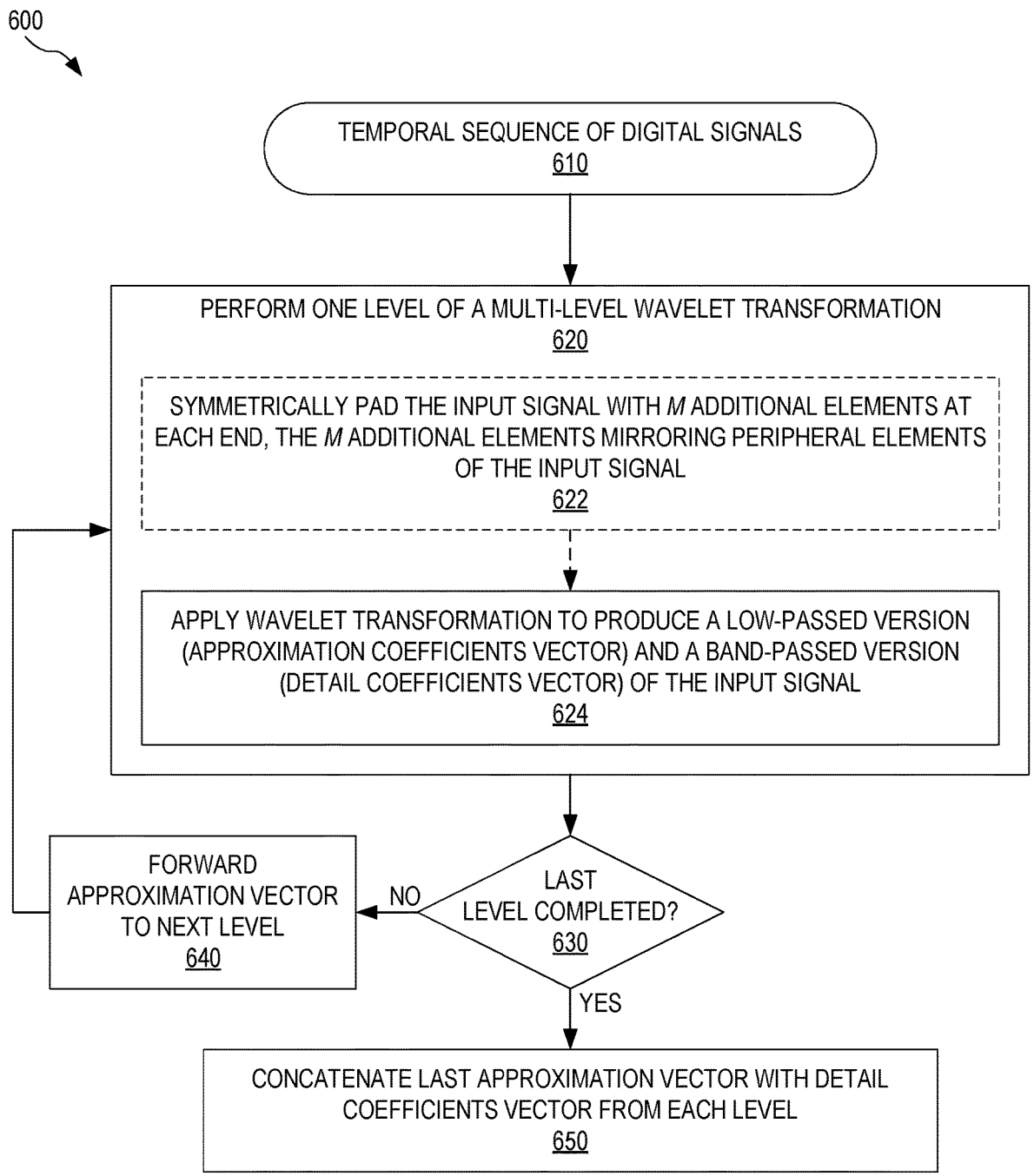
FIG. 6 illustrates a method for compressing physiological data using a multi-level discrete wavelet transformation, according to an embodiment.

FIG. 6 illustrates one method 600 for compressing physiological data using a multi-level DWT. Method 600 is an embodiment of step 520 of method 500. Method 600 may be encoded in compression instructions 432 as wavelet transformation instructions 434.

Steps 620 and 630 are repeated iteratively to apply a recursive multi-level DWT to the temporal sequence of digital signals. The recursive multi-level DWT is based on the Daubechies wavelet family. The Daubechies wavelet family is characterized by a set of scaling and wavelet coefficients that have low-passing and band-passing characteristics similar to that of quadrature mirror filters:

$$A[n] = (x*h_0)[n] = \sum_{k=-\infty}^{\infty} x[k]h_0[n-k],$$

$$D[n] = (x*h_1)[n] = \sum_{k=-\infty}^{\infty} x[k]h_1[n-k],$$

wherein x[n] is the input vector, h[n] is the wavelet basis, n is an index indicating each entry of the associated vector, A is the scaling coefficient vector, D is the wavelet coefficient vector, and $h_0$ and $h_1$ are the Daubechies (db3) scaling and wavelength coefficients, respectively. $h_0$ and $h_1$ may be encoded in wavelet transformation instructions 434 as Daubechies coefficients 435.

The recursive multi-level DWT of method 600 has at least two levels. In one implementation, the number of levels is in the range between three and six so as to decompose the temporal sequence of digital signals with sufficient time and spectral resolution, without imposing overdue computational complexity. In one example, the number of levels is four.

Each iteration of step 620 applies a respective level of the recursive multi-level DWT to a respective input vector. The input to the first iteration of step 620 is an input vector 610. Input vector 610 contains the temporal sequence of digital signals, e.g., temporal sequence 294. Step 620 includes a step 624 of applying a DWT to the temporal sequence of digital signals to produce a low-passed version and a band-passed version of the temporal sequence of digital signals. The low-passed version is a vector of approximation coefficients, also referred to herein as an approximation coefficients vector $A_L$. The band-passed version is a vector of detail coefficients, also referred to herein as a detail coefficients vector $D_L$, wherein L is the iteration (or level) number. For each iteration of step 620 after the first iteration, the input vector to step 620 is the approximation coefficients vector $A_L$ generated by step 624 of the preceding iteration. In other words, each iteration L of step 624 calculates:

$$A_{L+1}[n] = \sum_{k=0}^{5} h_0[k] A_L[2n+k],$$

$$D_{L+1}[n] = \sum_{k=0}^{5} h_1[k] A_L[2n+k],$$

wherein $h_0=h_0[0]$, $h_0[1]$, . . . , $h_0[5]$, and $h_1=h_1[0]$, $h_1[1]$, . . . , $h_1[5]$ are the Daubechies (db3) scaling and wavelet coefficients, respectively, with $\|h_{0,1}\|_2^2=1$.

After completion of each iteration of step 620, method 600 proceeds to step 630. Step 630 is a decision step. If the last level of the recursive multi-level DWT is completed method 600 proceeds to a step 650. If not, method 600 proceeds to step 640. Step 640 forwards the approximation coefficients vector $A_L$ generated by the most recent iteration of step 624 to the next iteration of step 620 to be used as the input vector thereto.

Step 650 concatenates the approximation coefficients vector $A_L$ of the last iteration (or level) of step 620 with the detail coefficients vector $D_L$ of each iteration (or level) of step 620. The output of step 650 is the resulting concatenated vector W. In the example where L=4, step 650 concatenates the vectors $A_4$, $D_4$, $D_3$, $D_2$, and $D_1$.

Figure 7:
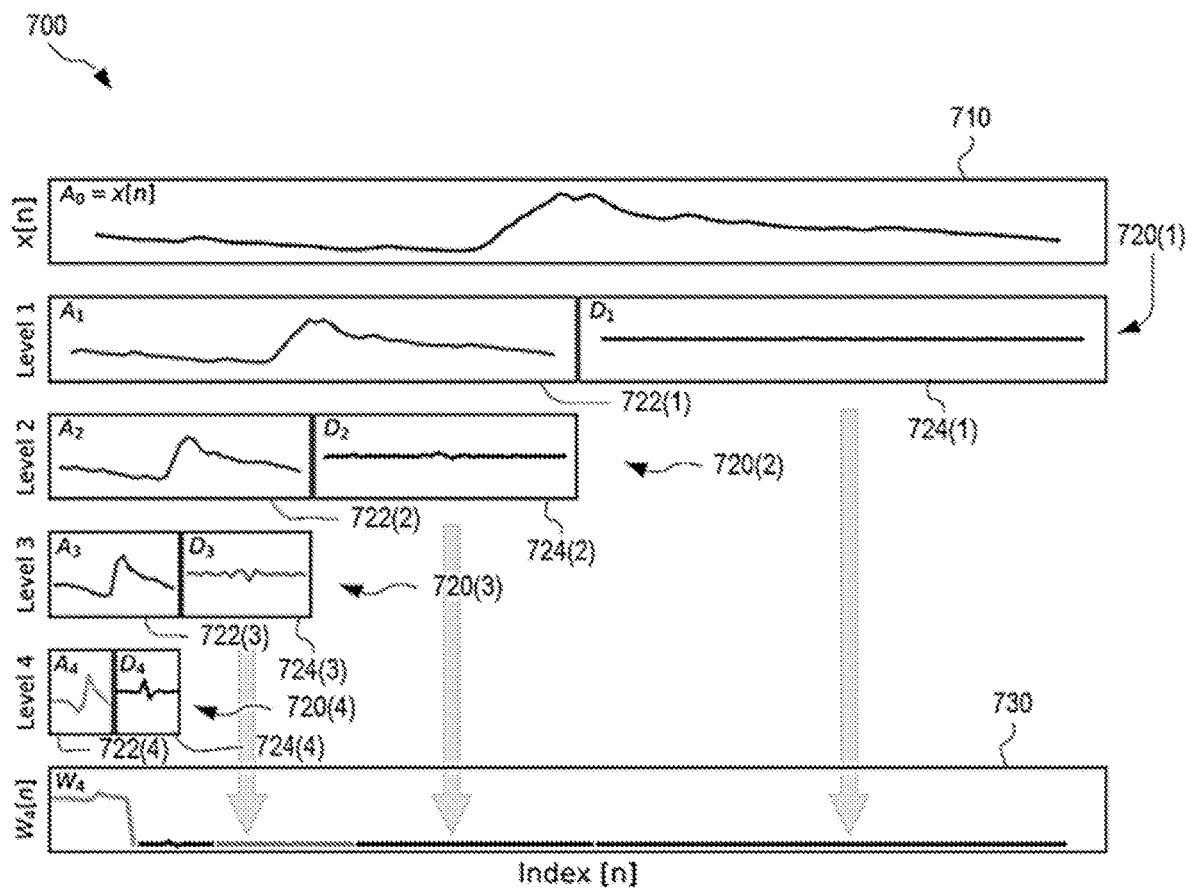
FIG. 7 illustrates a four-level example of the method of FIG. 6.

FIG. 7 illustrates a four-level example of method 600. The first iteration of step 620 receives, as its input vector, a vector $A_0=x[n]$ (labeled 710). Vector 710 is a temporal sequence of digital signals. The first iteration of step 620 generates an output 720(1) that includes approximation coefficients vector $A_1$ (reference numeral 722(1)) and detail coefficients vector $D_1$ (labeled 724(1)). The second iteration of step 620 takes approximation coefficients vector $A_1$ as its input vector and generates an output 720(2) that includes approximation coefficients vector $A_2$ (labeled 722(2)) and detail coefficients vector $D_2$ (labeled 724(2)). The third iteration of step 620 takes approximation coefficients vector $A_2$ as its input vector and generates an output 720(3) that includes approximation coefficients vector $A_3$ (labeled 722(3)) and detail coefficients vector $D_3$ (labeled 1 724(3)). The fourth and last iteration of step 620 takes approximation coefficients vector $A_3$ as its input vector and generates an output 720(4) that includes approximation coefficients vector $A_4$ (labeled 722(4)) and detail coefficients vector $D_4$ (labeled 724(4)). At each level L, the length of each of approximation coefficients vector $A_L$ and detail coefficients vector $D_L$ is half the length of approximation coefficients vector $A_{L-1}$. The output of step 650 is the concatenated vector $W_4$ composed of vectors $A_4$, $D_4$, $D_3$, $D_2$, and $D_1$. The coefficients in $W_4$ represent a multi-scale DWT of the original temporal sequence $A_0$ and contain all the information needed to completely reconstruct $A_0$ using the inverse wavelet transformation.

The band passing nature for each transform level is evident in FIG. 7, where short-term ('high-frequency') variations are captured in the detail coefficients vector $D_L$ in the earlier transformation levels, whereas long-term ('low-frequency') variations are captured in the detail coefficients vector $D_L$ in the later transform levels.

In one scenario, $W_4$ is produced from a temporal sequence of digital EDA signals. In this scenario, $D_4$, $D_3$, $D_2$, and $D_1$ are employed to contain phasic features of the EDA signal whereas $A_4$ contains tonic features of the EDA signal.

Referring again to FIG. 6, step 620 may include a step 622, performed prior to step 624, of symmetrically padding the input signal with M additional elements at each end. The M additional elements mirror peripheral elements of the input signal. Given an input vector $A_L$ of length N, step 622 applies a Pad( ) function that will return a new vector, $A_{pad,L}$. $A_{pad,L}$ is a copy of $A_L$ with four additional elements on the left and right sides that mirror the perimeter elements of $A_L$, such that:

$$A_L=[x_0, x_1, \ldots, x_{n-1}],$$

$$A_{pad,L}=[\ldots, x_1, x_0, |x_0, x_1, \ldots, x_{n-1}| x_{n-1}, x_{n-2}, \ldots]$$

The length of $A_{pad,L}$ is N+2M. In one implementation, M=4, which results in two additional coefficients being generated (one coefficient on each end) during the DWT of step 624. The padding in step 622 prevents the generation of large coefficients at the signal borders that otherwise can lead to reconstruction errors if omitted in the compression process. In an alternative embodiment, step 622 is replaced by a different padding scheme, such as zero-padding or periodic-padding. However, we have found that the symmetrical padding of step 624 leads to lower reconstruction errors at least when the physiological parameter sensed is EDA signal.

"Algorithm 1", below, lists source code for one example of step 620 that implements steps 622 and 624:

| Algorithm 1 ML-DWT Algorithm | | |
|---|---|---|
| Input: x | | ▶len(x)=128 |
| Output: $W_4$ | | ▶len($W_4$)=145 |
| 1: | procedure ML-DWT | |
| 2: | $A_L = [x_0, x_1, \ldots, x_{127}]$ | |
| 3: | $h_0 = [h_{0,0}, h_0,1, \ldots, h_{0,5}]$ | |
| 4: | $h_1 = [h_{1,0}, h_1,1, \ldots, h_{1,5}]$ | |
| 5: | repeat | |
| 6: | $A_{pad} = \text{PAD}(A_L)$ | |
| 7: | L = L + 1 | |
| 8: | $A_L, D_L = \text{WT}(A_{pad}, h_0, h_1)$ | |
| 9: | until L=4 | |
| 10: | $W_4[0:11] = A_4$ | |
| 11: | $W_4[12:23] = D_4$ | |
| 12: | $W_4[24:43] = D_3$ | |
| 13: | $W_4[44:78] = D_2$ | |
| 14: | $W_4[79:144] = D_1$ | |
| 15: | return $W_4$ | |
| 16: | end procedure | |
| 17: | function PAD(A) | |
| 18: | N = len(A) | |
| 19: | M = N + 8 | |
| 20: | $A_{pad}[0:M-1] = \{0, 0, \ldots, 0\}$ | |
| 21: | $A_{pad} = [X3, X2, X1, X0, X0, X1, \ldots$ $\ldots, x_{N-2}, x_{N-1}, x_{N-1}, x_{N-2}, x_{N-3}, x_{N-4}]$ | |
| 22: | return $A_{pad}$ | |
| 23: | end function | |
| 24: | function WT($A_L$, $h_0$, $h_1$) | |
| 25: | N = len(AL) | |
| 26: | M = N/2 | |
| 27: | $A_{L+1}[0:M-1] = \{0, 0, \ldots, 0\}$ | |
| 28: | $D_{L+1}[0:M-1] = \{0, 0, \ldots, 0\}$ | |
| 29: | for i = 0 to M − 1 do | |

| Algorithm 1 ML-DWT Algorithm |
| --- |
| 30:     for j = 0 to 5 do |
| 31:         $A_{L+1}[i] = A_{L+1}[i] + h_0[j]A_L[2i + j]$ |
| 32:         $D_{L+1}[i] = A_{L+1}[i] + h_1[j]A_L[2i + j]$ |
| 33:     end for |
| 34:   end for |
| 35:   return AL+1, DL+1 |
| 36: end function |

Algorithm 1 may be encoded in wavelet transformation instructions 434.

Figure 8:
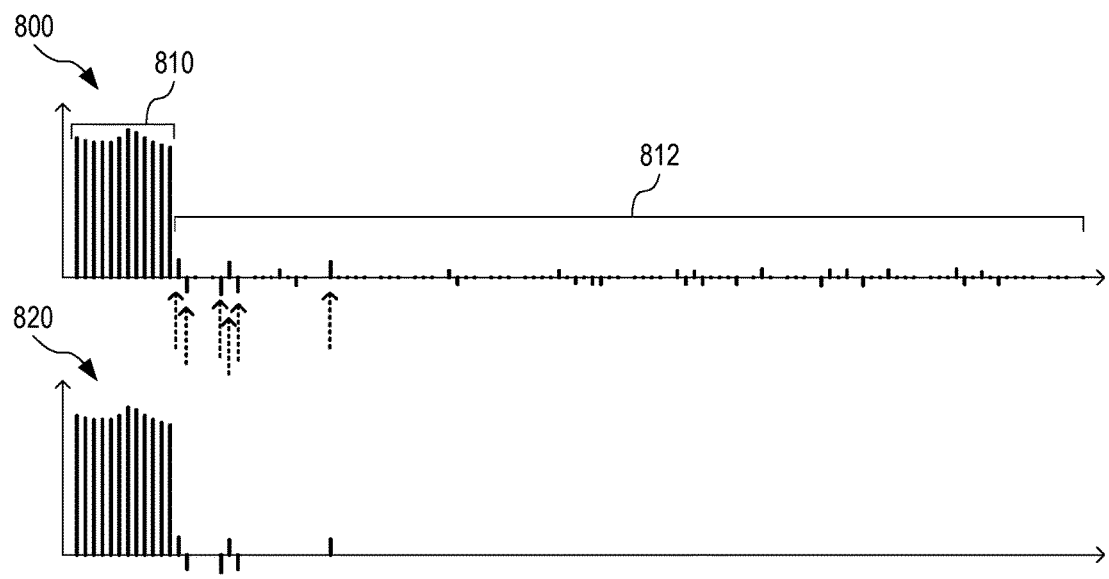
FIG. 8 illustrates one example of data compression performed the method of FIG. 5.

FIG. 8 illustrates one example of the data compression performed in one embodiment of step 530 of method 500 that includes step 532. The example depicted in FIG. 8 is based upon transformation coefficients similar to those of $W_4$ of FIG. 7. In this example, the input to step 530 is a vector 800 the includes an approximation coefficients portion 810 and detail coefficients portion 812. Approximation coefficients portion 810 is an example of $A_4$ of FIG. 7. Detail coefficients portion 812 is an example of a concatenation of $D_4$, $D_3$, $D_2$, and $D_1$ of FIG. 7. Step 532 retains all transformation coefficients of approximation coefficients portion 810 but only a subset of the transformation coefficients of detail coefficients portion 812. The retained subset contains largest-magnitude transformation coefficients of detail coefficients portion 812 (indicated by dashed arrows in FIG. 8. The resulting output is the transformation coefficients shown in vector 820. In an alternative example, some of the transformation coefficients of approximation coefficients portion 810 are of lesser magnitude than some of the transformation coefficients of detail coefficients portion 812, and step 532 omits at least some of the lesser-magnitude transformation coefficients of approximation coefficients portion 810.

The examples shown in FIGS. 7 and 8 illustrate that significant compression may be achieved without much loss of information when the complete set of transformation coefficients (prior to compression) is "sparse", that is, has many near-zero values and only a relatively small number of transformation coefficients of significant magnitude.

More generally stated, step 532 of method processes an input vector W of N transformation coefficients to produce a compressed vector $\hat{W}$ of transformation coefficients that contains only K transformation coefficients from W. N and K are positive integers and N>K. For example, when the input to step 532 is $W_4$, step produces an output vector $\hat{W}_4$ that contains only a subset of the transformation coefficients of $\hat{W}$. In one embodiment, K is a predefined number. In another embodiment, step 530 evaluates the transformation coefficients of W to determine the value of K. For example, step 530 may retain only transformation coefficients of detail coefficients vectors $D_L$ (or of input vector W) having magnitude greater than a predefined threshold magnitude. In one implementation, N/K>5. For example, N=145 and K=16. Step 532 may implement a sorting routine to select $\hat{W}$ from W.

Figures 9, 10:
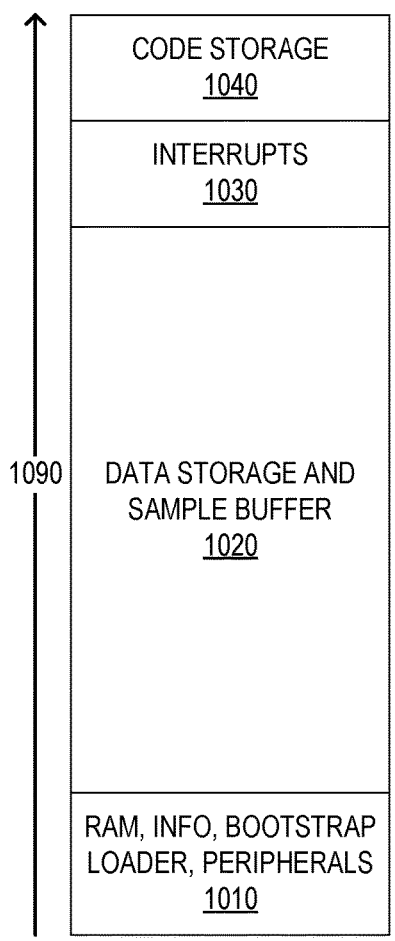
FIG. 9 illustrates encoding, in memory, of an example set of compressed transformation coefficients, according to an embodiment.
FIG. 10 illustrates an allocation scheme of the non-volatile memory of FIG. 2, according to an embodiment.

"Algorithm 2", below, lists source code for one example of steps 530 and 540 to compress $W_4$ of length 145 (e.g., produced by Algorithm 2) to produce $\hat{W}_4$ of length 16 and encode $\hat{W}_4$ in one example of data storage 222 as shown in FIG. 9.

| Algorithm 2 ML-DWT Compression |
| --- |
| Input: $W_4$, K |
| Output: $\hat{W}_4$ |
| 1: procedure COMPRESSION($W_4$, K) |
| 2:   LSI = ARGSORT(W4, K) |
| 3:   $\hat{W}_4$ = ENCODE($W_4$, LSI) |
| 4:   return $\hat{W}_4$ |
| 5: end procedure |
| 6: function ARGSORT($W_4$, K) |
| 7:   LSI = { } |
| 8:   max = 0 |
| 9:   for j = 0 to K − 1 do |
| 10:     for j = 0 to 144 do |
| 11:       if i exists in LSI then |
| 12:         continue |
| 13:       end if |
| 14:       if abs(W[i]) > abs(max) then |
| 15:         max = W[i] |
| 16:         index = i |
| 17:       end if |
| 18:     end for |
| 19:     LSI[j] = index |
| 20:     index, max = 0 |
| 21:   end for |
| 22:   return LSI |
| 23: end function |
| 24: function ENCODE($W_4$, LSI) |
| 25:   for i = 0 to 11 do   ▶$A_4 = W_4[0:11]$ |
| 26:     A [i] = $W_4$ [i] << 4   ▶left bit-shift |
| 27:   end for |
| 28:   for j = 12 to K − 1 do   ▶$D \in W_4 [12:144]$ |
| 29:     D[j − 12] = W4[LSI[j]] |
| 30:   end for |
| 31:   for k ∈ {0, 2, 4, 6} do |
| 32:     A[j] = A[j] ( LSI[j] & 0x000F) |
| 33:     A[j + 1] = A[j + 1] ((LSI[j] >> 4) & 0x000F) |
| 34:   end for |
| 35:   return $\hat{W}_4$ |
| 36: end function |

The ARGSORT( ) function of Algorithm 2 may be encoded in coefficient selection instructions 436. The ENCODE( ) function of Algorithm 2 may be encoded in encoding instructions 438. The $A_4$ coefficients are represented using unsigned, 12-bit values (in this example, temporal sequence 294 has all positive values). The present example of data storage 222 has 16-bit architecture, so the $A_4$ coefficients can be encoded in the 12 most significant bits within a 16-bit memory register, shown in the ENCODE( ) function of Algorithm 2 (step 25). The detail coefficients can be positive or negative and are represented using a signed, 8-bit integer (step 28). The addresses of each D coefficient, D.addr, range from 12-144 and are encoded with 8-bits. The D.addr values are split into 2, 4-bit segments where they can be stored alongside the $A_4$ coefficients (steps 31 and 32), as shown in FIG. 9. In certain scenarios, the $A_4$ coefficients are always in the top 12 largest coefficients, and there is no need to store their location if they are encoded in their original order. The compressed vector $\hat{W}_4$ of FIG. 9 is an optimized data structure for a 16-bit architecture and helps extend long-term monitoring capabilities.

FIG. 10 illustrates one allocation scheme 1000 of non-volatile memory 220 as a function of address 1090 of memory registers. Allocation scheme 1000 allocates different segments of memory 220 to (a) RAM, info, bootstrap loader, and peripherals (segment 1010), (b) data storage 222 and sample buffer 216 (segment 1020), (c) interrupts (segment 1030), and (d) code storage 230 (segment 1040). In one example, allocation scheme is applied to a 48 kilobyte embodiment of memory 220, segment 1010 spans from address 0x00000 to address 0x04400, segment 1020 spans from address 0x04400 to address 0x0FF80, segment 1030 spans from address 0x0FF80 to address 0x10000, and segment 1040 spans from address 0x10000 to address 0x12700.

Example 1: Electrodermal Activity Study

Measures associated with EDA are typically grouped into two classes of tonic and phasic features. Tonic EDA measures, relating to the slowly varying skin conductance level, may be used as an indicator of arousal in psychophysiological research.

Figure 11:
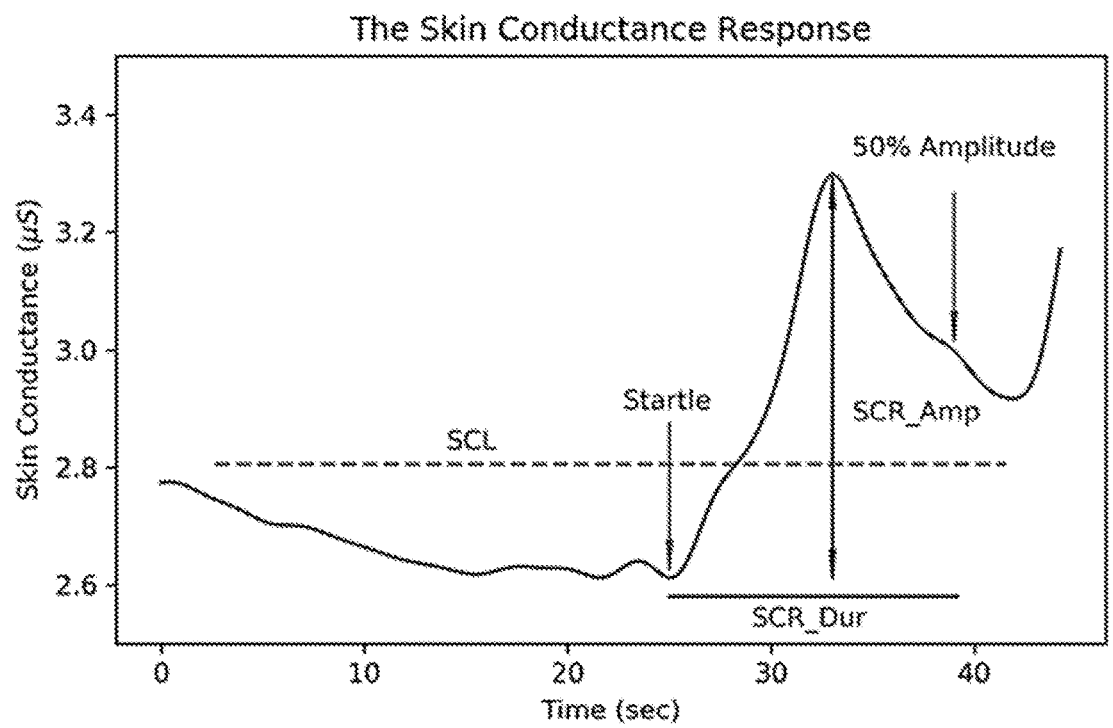
FIG. 11 shows examples of features of skin conductance response in EDA sensing.

Materials and Methods:

FIG. 11 shows features of skin conductance response (SCR). The skin conductance level (SCL) was computed as the average skin conductance (SC) value across a 64 second window. SCR_Dur is the time from the beginning of the SCR to the 50% amplitude level. SCR_Amp is the amplitude from the minimum to the maximum of an SCR.

The tonic features shown in FIG. 11 are the average skin conductance level (SCL), the standard deviation of the EDA signal (EDA_Std), the signal maximum amplitude (SC_Max) and minimum (SC_Min). Phasic features relate to the rapid fluctuations of skin conductance (SC) in response to a stimulus and may be helpful in (a) evaluating stress and anxiety, (b) evaluating orienting response, and (c) applications related to emotional sensing. These skin conductance responses (SCRs) have both an SC amplitude (SCR_Amp), measured from the trough to peak of a SC pulse, and a duration (SCR_Dur), measured as the time between the onset of an SCR to the point when the SC level reaches 50% of its peak amplitude. The area under the curve of an SCR (SCR_AUC) is measured according to SCR_AUC=½ SCR_Amp×SCR_Dur to provide a relative estimate of an SCR size. Studies involving EDA may be interested in the psychophysiological response to emotional stimuli which can vary depending on the measurement location. Sweat glands concentrations are not evenly distributed across the body, with the largest densities being measured on the soles of the feet (620/cm2), the forehead (360/cm2), the palms and cheeks (300/cm2), and the thighs (120/cm2) and not all measurement locations are equally responsive to emotional stimuli. It has been reported that emotional sweating can be recorded at measurement sites other than the palmar and plantar surfaces but often at a reduced amplitude and activation levels. In this study, EDA is measured at the wrist, using device 100 implemented in wristband 104, since the form factor of wrist-worn biosensors is commonly accepted in commercial devices and bracelets provide good mounting surfaces for attaching electrodes to the skin. Device 100 could be further miniaturized to record EDA at the palmar surfaces (where SCR activity is more prominent) without being obtrusive or encumbering daily activity.

Figure 12:
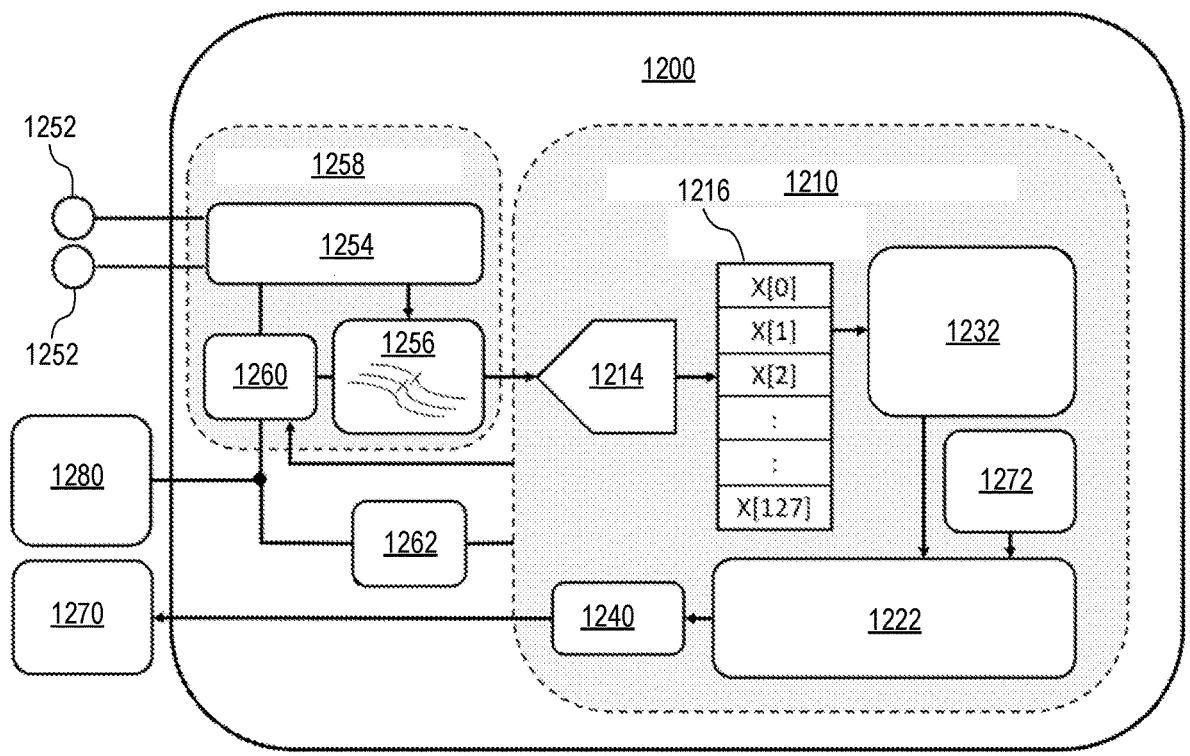
FIG. 12 is a functional block diagram of a low-resource biosensor, according to an embodiment.

FIG. 12 is a functional block diagram of a low-resource biosensor 1200 used in the present study. Biosensor 1200 was implemented in a wearable device 1302 shown in FIG. 13. Wearable device 1302 includes a wristband 1322 that houses biosensor 1200. Biosensor 1200 is configured to perform method 500 (including steps 502 and 504). Biosensor 1200 includes a microcontroller 1210 and an analog front end (AFE) 1258. Microcontroller 1210 is an example of microcontroller 310. Microcontroller 1210 implements memory 220 according to allocation scheme 900. Microcontroller 1210 includes (a) data compression instructions 432 implemented according to method 600, Algorithm 1, Algorithm 2, and FIG. 9. AFE 1258 is an example of analog front end 258.

Figure 13:
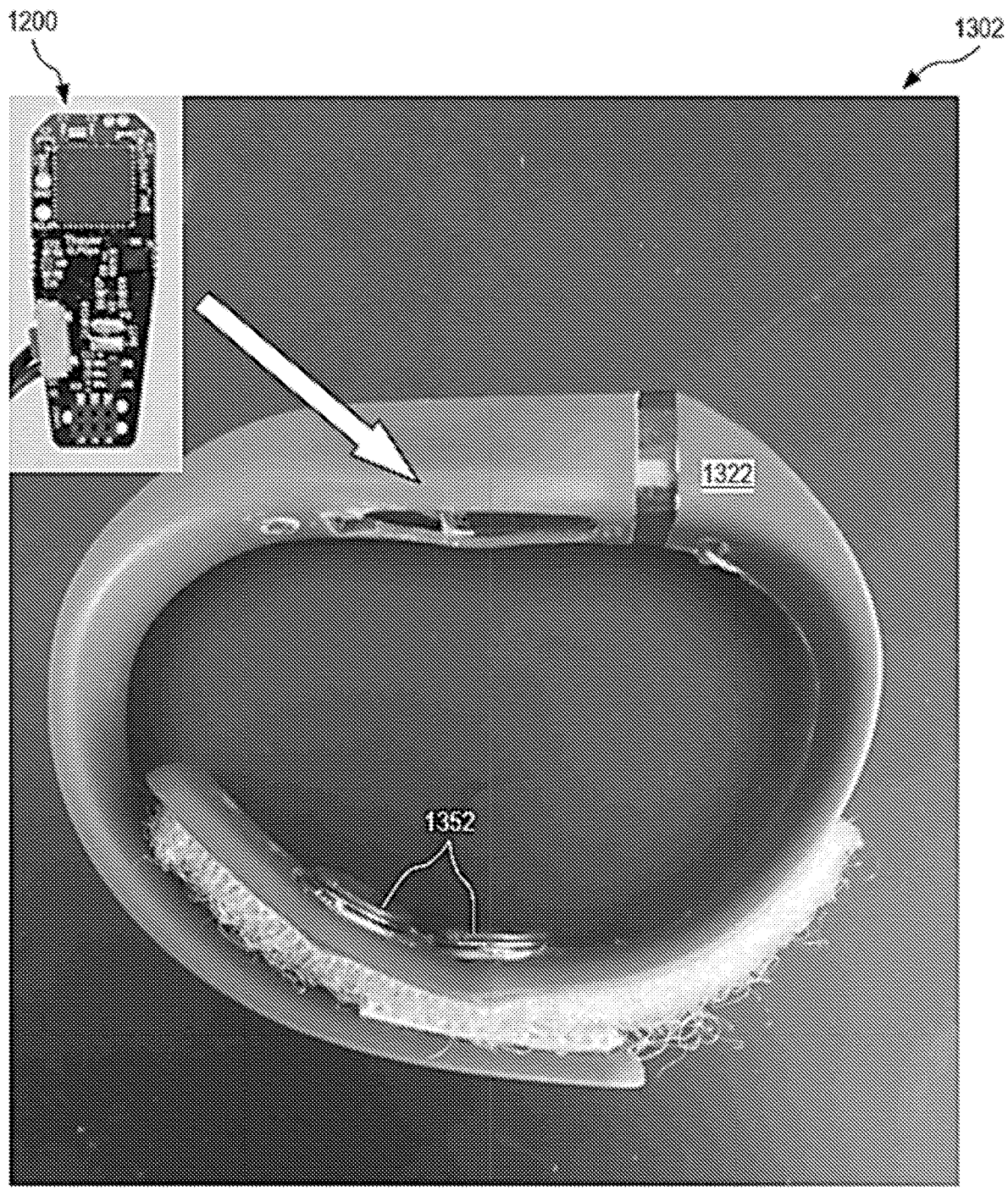
FIG. 13 shows the biosensor of FIG. 12 implemented in a wearable device, according to an embodiment.

AFE 1258 includes an EDA amplifier 1254 followed by a 4th order low pass filter (LPF) 1256. LPF 1256 (discussed in further detail below in reference to FIG. 23) was designed to pass the EDA signal from 0-1 Hz since the frequency response of sympathetic activities for physical and cognitive stress fall below 0.25 Hz. EDA amplifier 1254 measures electrodermal activity at the ventral wrist using a single op-amp (Analog Devices, AD8603, Norwood, MA, USA) topology. This topology (discussed in further detail below in reference to FIG. 22) uses a quasi constant-current model for skin conductance measurement. The 1 cm diameter Ag/AgCl electrodes 1352 (Thought Technologies LLC, Montreal, QC, Canada) are replaceable and snap into place on the inside of wristband 1322 as shown in FIG. 13. Electrodes 1352 are mounted using 1.5 cm center-to-center spacing. AFE 1258 is powered by a low-noise voltage regulator at 2.8 V (Texas Instruments, LP5907) that can be powered down when no skin contact is detected.

Microcontroller 1210 is an ultra-low power, 16-bit embedded microcontroller (Texas Instruments, MSP430FR5969, Dallas, TX, USA) for digital signal processing and on-board data storage of the EDA signal. The MSP430 is regulated at 2.8 V with a low-noise linear voltage regulator 1262 (Texas Instruments, LP5907, Dallas, TX, USA) supplied by a rechargeable 3.7 V, 40 mAh lithium ion battery 1280 (Sparkfun, PRT-13852, Niwot, CO, USA). We used an interrupt-based embedded code model to set the MSP430 in ultra low-power mode between intervals of sampling and signal processing. The EDA signal is sampled at 2 Hz from AFE 1258 using a 12-bit ADC 1214 on the MSP430. EDA data are stored into a sample buffer 1216 before being compressed. All signal compression is conducted in real time and compressed EDA data are saved into a data storage 1222. A 48 KB FRAM on the MSP430 is allocated according to allocation scheme 1000, such that sample buffer 1216 and data storage 1222 are both within the 48 KB FRAM. Microcontroller 1210 includes a DWT+ compression block 1232 that utilizes the CPU of the MSP430 together with machine-readable instructions encoded in the 48 KB FRAM. Microcontroller 1210 further includes a universal asynchronous receiver-transmitter (UART) serial interface 1240 (an example of output interface 240). Timing for real-time clock 1272 and ADC 1214 is maintained using an external crystal oscillator at 32.768 kHz (not shown in FIG. 12). All signal processing in active mode is performed at 1 MHZ.

To extend device lifetime, we also designed a user-configurable periodic sampling scheme. At the beginning of each recording session, the device can be programmed to continuously record EDA or periodically record 64 s windows of EDA starting at any integer multiple of the on-board real time clock (RTC) minute register. By adjusting the number of minutes between sample windows, users can extend battery life and long-term storage capabilities of the 16-bit microcontroller.

Figure 14:
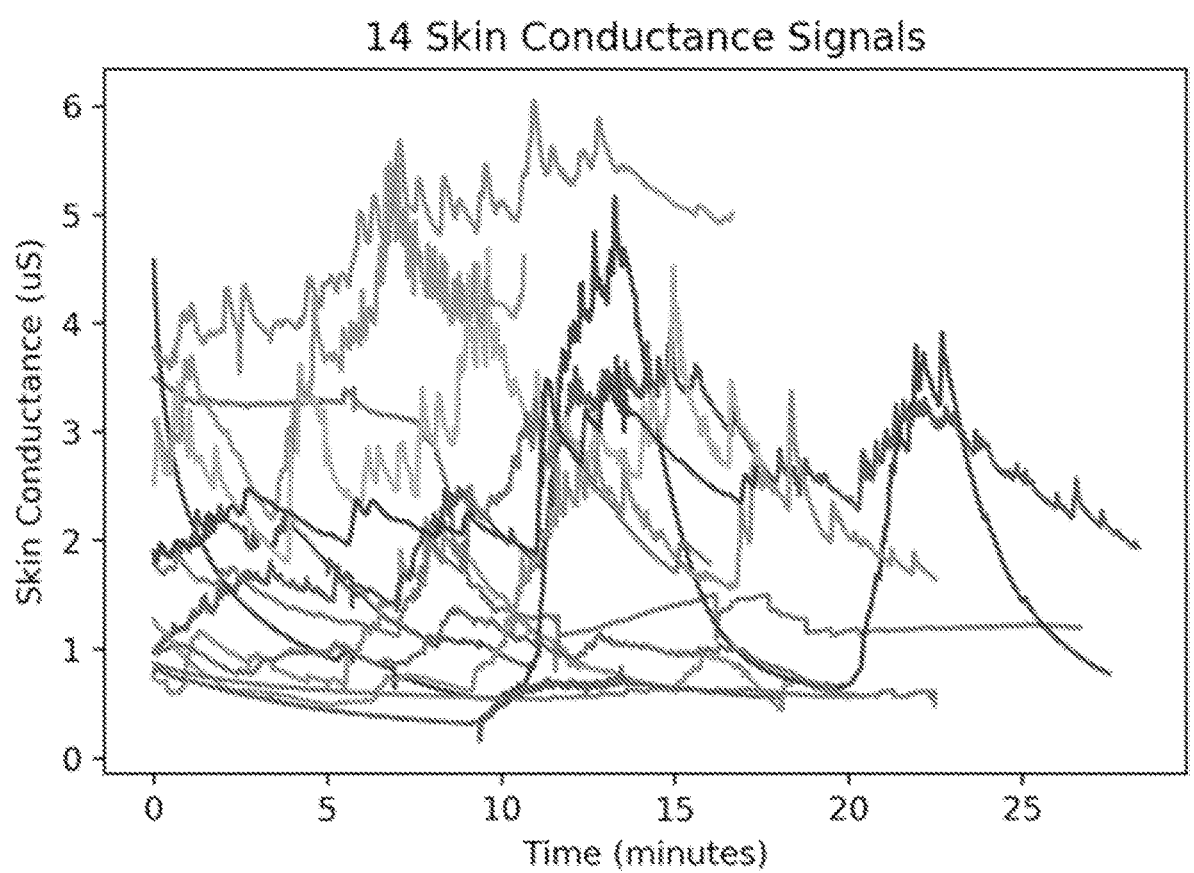
FIG. 14 shows EDA signals recorded during a stress induction protocol.

Encoding the $W_4$ coefficients was optimized by determining the expected range and sign of wavelet coefficients produced from applying the ML-DWT procedure on a collection of EDA signals shown in FIG. 14. These EDA signals were recorded during a stress induction protocol conducted across 14 participants (7 male and 7 female) with ages ranging from 24-36 years of age (average age: 27.6 year: median age: 26.5 year: std: 3.57 year). The 14 EDA signals were subdivided into 253 segments each representing 64 s of EDA.

Each participant wore the EDA sensor on their right wrist and remained in a seated position while being subjected to a series of tests known to simulate every day stressors. Each stress induction test began with 10 min of relaxation to establish a baseline EDA measurement without stress. When the initial rest period was over, the participant was exposed to a stress induction period lasting 4 min. There were three different stress induction methods: an auditory startle (periodically dropping a textbook on the floor while the participant sat quietly with their eyes closed), a mental arithmetic test (counting backwards from 500 in steps of 7), and public speaking (reciting William Faulkner's acceptance speech for the Nobel Prize in front of laboratory staff). Each stress induction period was followed by a 5 min period of rest. The order of stress induction tests were randomized and participants conducted anywhere from one to two stress induction tests (with 5 min of rests in between), depending on their willingness to participate in the full experiment. EDA data recordings were visually inspected and data segments having 'flat-line' skin conductance values below 0.01 µS, assumed as having poor or no electrode contact with the skin, were removed from the dataset (ex. data collected before the electrodes are attached to the body). In this way, the compression performance and signal distortion of the new ML-DWT compression algorithm is analyzed only from quality EDA signals recorded in a controlled environment during a stress-induction protocol. These signals were filtered using a Chebyshev type-II filter (0.6 Hz passband at 3 dB: 0.9 Hz stopband at 74 dB) before being compressed. All EDA signals were subdivided into 64 s windows for the evaluation, resulting in 253 independent EDA signals. These recordings are mainly used to characterize the expected performance of an EDA compression algorithm when applied across a population experiencing relaxation and induced stress.

Before performing the ML-DWT, the skin conductance values in x are converted from units of 1 µS to units of 0.01 µS so that the $W_4$ coefficients can be cast from Q15.16 format (1 signed bit: 15 integer bits: 16 fractional bits) into signed, 16-bit integers (Q15.0) and maintain a resolution of ±0.01 µS. Table 1, below, summarizes the minimum memory requirements to encode the $W_4$ coefficients by computing the maximum coefficient value in binary notation (bitwidth=$\log_2(\max(|X|))$ for $X \in \{A_4, D_4, D_3, D_2, D_1, LSI\}$).

TABLE 1

Wavelet coefficient memory requirements.

| WT Level | Max Value | Max Base 2 | Bits Required | Sign Bit? | Bitwidth Selected |
|---|---|---|---|---|---|
| $A_4$ | 2399.53 | 11.2285 | 12 | No | 12 |
| $D_4$ | 123.881 | 6.95281 | 7 | Yes | 8 |
| $D_3$ | 73.2285 | 6.1943 | 7 | Yes | 8 |
| $D_2$ | 43.2475 | 5.43454 | 6 | Yes | 8 |
| $D_1$ | 21.7329 | 4.44181 | 5 | Yes | 8 |
| LSI | 145 | 7.17991 | 8 | No | 8 |

Figure 15A:
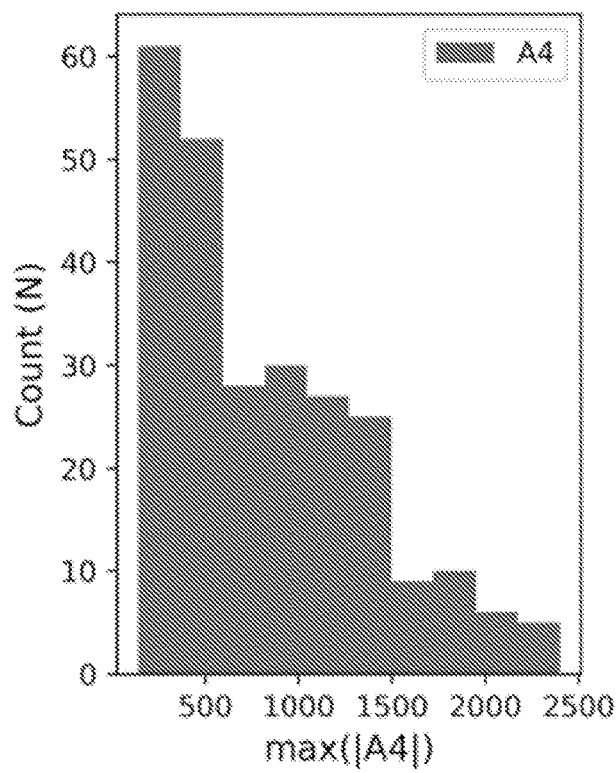
FIGS. 15A and 15B shows magnitudes of transformation coefficients in an example of a multi-level discrete wavelet transformation.
Figure 15B:
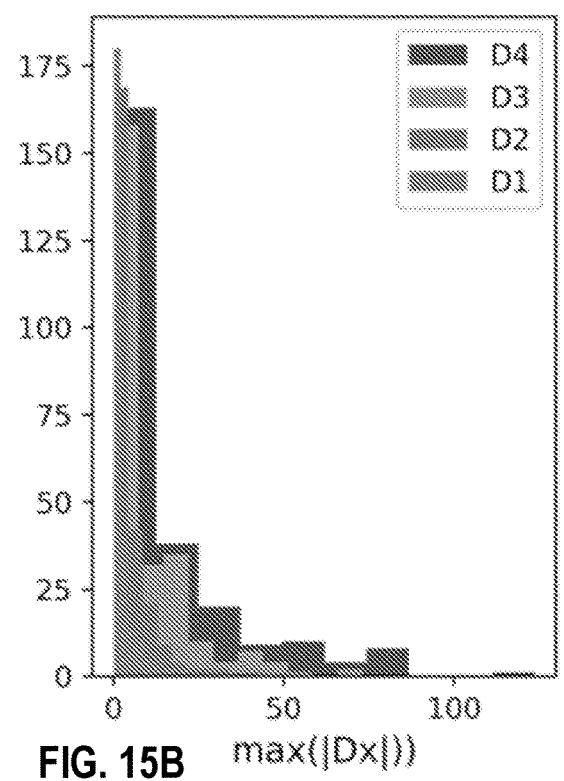

The magnitudes for each ML-DWT coefficient computed from the EDA signals of FIG. 14 are shown in FIGS. 15A and 15B. These histograms were used to determine the maximum bits needed to represent the $W_4$ coefficients in binary notation. The final required bitwidths to store the $W_4$ coefficients and the LSI are summarized in the last column of Table 1 which defines the data structure to be encoded as shown in FIG. 9.

The compressed EDA signal was downloaded to an external device 1270 via UART serial interface 1240 for reconstruction. The original EDA signal, x, was reconstructed from $W_4$ by populating an empty $W_4$ vector with the coefficients retained in $\hat{W}_4$ and filling the remaining values with zeros. The symmetric signal extension described earlier was designed to use Python's PyWavelet library (https://github.com/PyWavelets) for reconstructing the EDA signal from $W_4$ using the inverse DWT function, pywt.waverec( ).

The compression ratio defines the memory savings achievable with the ML-DWT implementation used in this example and is expressed as:

$$CR = \frac{N_x}{N_{wt} + N_i},$$

where $N_x$, $N_{wt}$, and $N_i$ are the number of bits used to encode the EDA signal, the wavelet transformation coefficients, and $W_4$ indices, respectively. Each EDA sample is represented using 32-bit fixed point floats (Q15.16) at a sample rate of 2 Hz, leading to an input data rate of 64 bits/s.

Lossy compression inevitably distorts the original signal during reconstruction when signal energy of the ML-DWT is omitted. We used the percent root mean square difference (PRD) to evaluate the distortion of the reconstructed EDA signals, which is defined as:

$$PRD(\%) = \frac{\sqrt{\sum_{i=0}^{N-1}(x(i) - \hat{x}(i))^2}}{\sqrt{\sum_{i=0}^{N-1}(x(i))^2}} \times 100.$$

The Root Mean Square Error (RMSErr) is also computed to enable a performance comparison between our wavelet-based compression method and a compressive sensing method presented by T. Chaspari, et al. in "Sparse representation of electrodermal activity with knowledge-driven dictionaries", IEEE Trans. Biomed. Eng. 2015, 62, 960-971.

$$RMSErr(\mu S) = \sqrt{\frac{1}{N}\sum_{i=0}^{N-1}(x(i) - \hat{x}(i))^2}.$$

In both equations, x and $\hat{x}$ represent the original and reconstructed signals, respectively, and N is the length of the uncompressed signal.

The energy compaction of the ML-DWT was evaluated by calculating the percentage of total signal energy (% Energy) contained within each approximation and detail coefficient vector of $W_4$ by:

$$\% \text{ Energy} = \frac{\sum_{i=0}^{n-1} c[i]^2}{\sum_{i=0}^{N-1} W_4[i]^2} \times 100,$$

$c \in \{A_4, D_4, D_3, D_2, D_1\}; n = \text{length } (c); N = 145,$ where c is an approximation or detail coefficient vector of length n and $W_4$ is the entire multilevel wavelet transformation vector of length N.

We hypothesized that, since a majority of signal energy is contained in a small number of coefficients, the EDA signal is well-suited for being compressed without significant loss of features associated with the signal. We evaluated this hypothesis by extracting common EDA features (as shown in FIG. 11) from the original and reconstructed signals and comparing the extracted features as a function of the CR.

For the phasic EDA features, the sum of the skin conductance response (SCR) amplitudes (Sum_Amp) and sum of the SCR durations (Sum_Dur) and their product, the Sum of the Area (Sum_AUC), were computed for each 64 s EDA signal using the third party algorithms provided by Taylor et al. in "Automatic identification of artifacts in electrodermal activity data", Proceedings of the 2015 37th Annual International Conference of the IEEE Engineering in Medicine and Biology Society (EMBC), Milan, Italy, 25-29 Aug. 2015: pp. 1934-1937. For each of the 253 EDA signals, the relative error (RE) for a given feature, f=(Sum_Amp, Sum_Dur, or Sum_AUC), was computed as follows:

$$R(f) = \frac{\sum_{i=1}^{253} f_{recon}, i - \sum_{i=1}^{253} f_{orig}, i}{\sum_{i=1}^{253} f_{orig}, i},$$

where $f_{orig}$ and $f_{recon}$ are features extracted from the original and reconstructed EDA signals, respectively. Additionally, the tonic features extracted from the EDA signal were the Skin Conductance Level (SCL or mean), minimum, maximum, and standard deviation for each EDA signal. The absolute error (in µS) between the original and reconstructed signal was used to evaluate the distortion.

Figure 16:
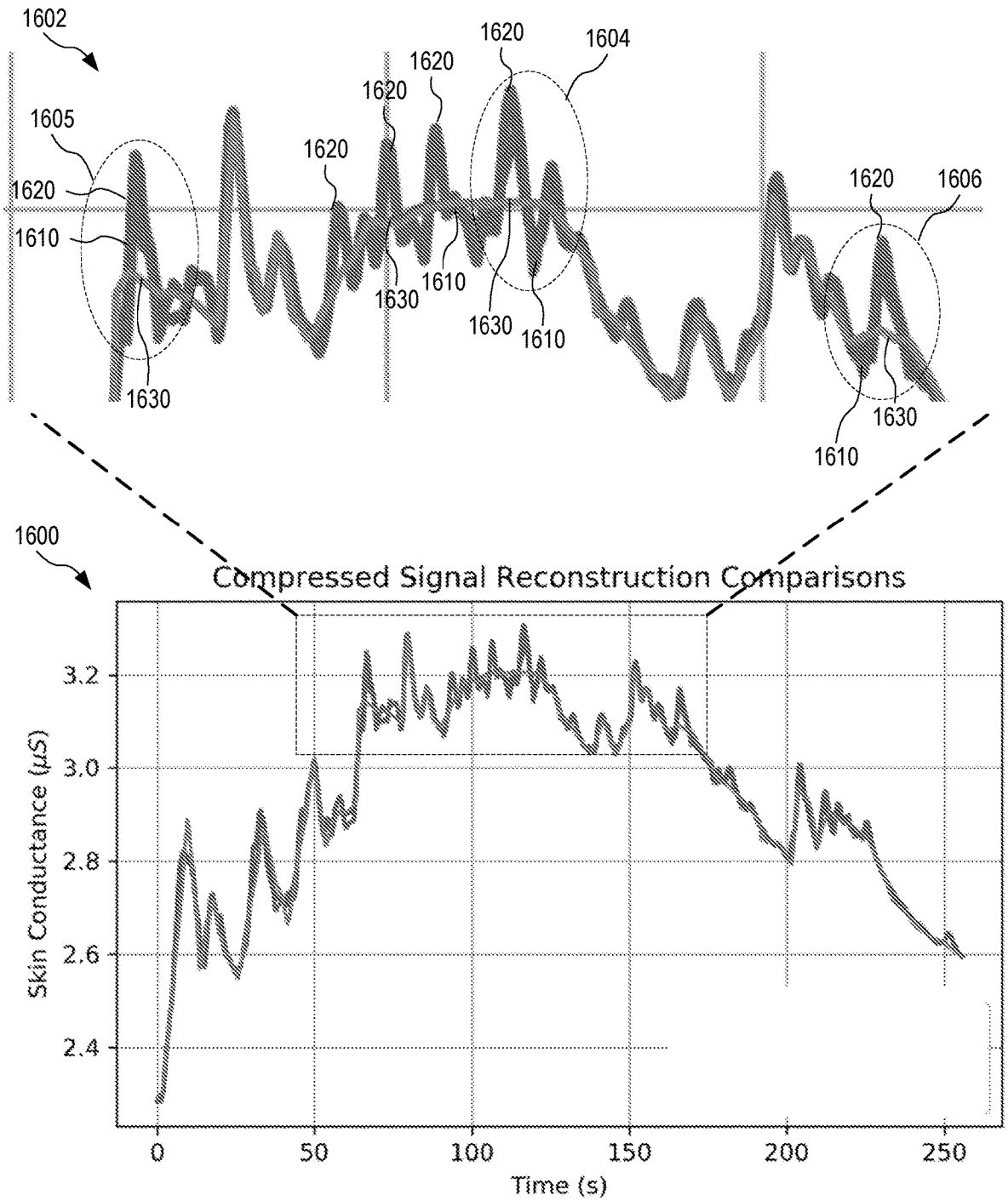
FIG. 16 compares reconstructed signals to the original electrodermal activity signal, in an example.

Results:

FIG. 16 compares reconstructed signals to the original EDA signal. FIG. 16 includes a complete plot 1600 and a close-up 1602 of a portion of plot 1600. A reconstructed signal 1610 from the compression method of the present example (as outlined above) is shown in FIG. 16, along with the original EDA signal 1620. A reconstructed signal 1630 based upon a modified version of the present compression method, retaining only 14 coefficients in $\hat{W}_4$ instead of 18, is shown as well to visually compare the reconstruction quality between the two methods. Both methods compress 64-s windows of EDA signals, consisting of 512 bytes each, into 30-byte encodings of $\hat{W}_4$ (CR=17.1×). In this way, any observable improvement in signal reconstruction quality is related to improvements of the algorithm's compression efficiency at encoding $W_4$ information into $\hat{W}_4$. Both reconstructed signal 1610 and reconstructed signal 1630 generally match original EDA signal 1620. However, as evident from regions 1604, 1605, and 1606 in close-up 1602, reconstructed signal 1610 more accurately follows the variations in original EDA signal 1620. Quantitatively, the encoding scheme in Algorithm 2, retaining 18 transformation coefficients, improves the RMSErr by 31.8% (from 0.0274 µS to 0.0208 µS) at the same compression ratio, as compared to the modified scheme retaining only 14 transformation coefficients.

Figure 17A:
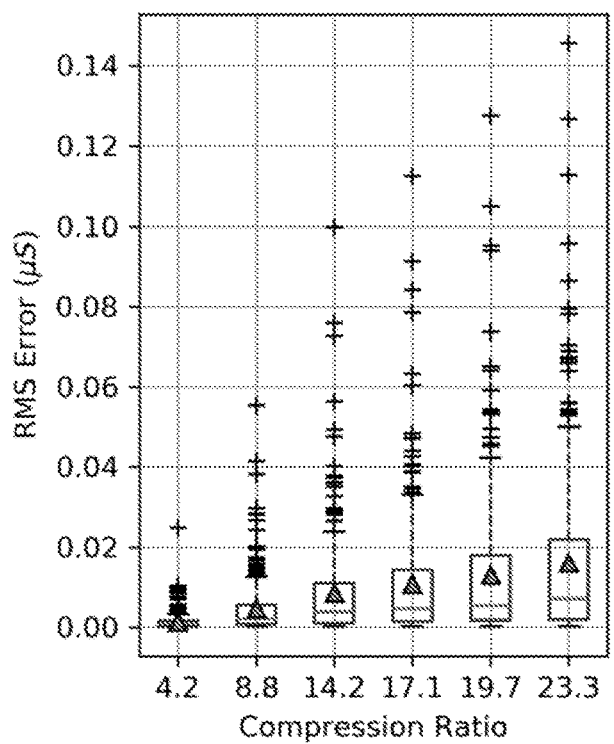
FIGS. 17A and 17B are plots of distortion metrics evaluating reconstruction accuracy, in an example.
Figure 17B:
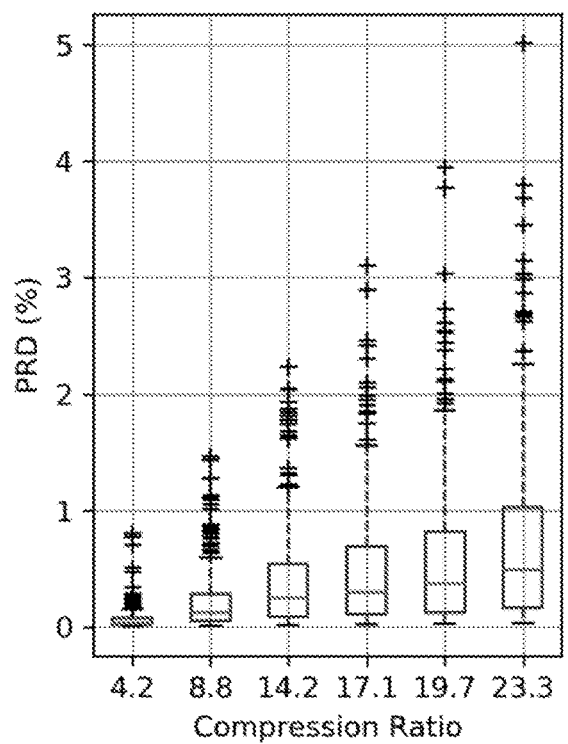

The distortion of the reconstructed signal is evaluated using the RMSErr and PRD distortion metrics, as defined above, to evaluate the quality of the compression process. FIG. 17A shows the RMSErr for each reconstruction over a range of compression ratios based on the 253 EDA signals from FIG. 14. FIG. 17A shows the root mean square error (RMSErr) of 253 EDA signals at a range of compression ratios. The mean RMSErr at each compression ratio is indicated by triangles. FIG. 17B shows the percent root mean square difference (PRD) distortion. The PRD is minimal for CRs below 14.2× while the upper quartile range remains below 1% for CRs up to 19.7×. For CRs up to 23.3×, the RMSErr is below 0.023 µS for 75% of all signals evaluated and the average RMSErr is no greater than 0.016 µS. For CRs up to 23.3×, the PRD is below 1.1% for 75% of the EDA signals evaluated. As the CR exceeds 23.3×, the PRD rapidly increases as coefficients from the $A_4$ vector are omitted.

The ML-DWT transformation tends to compact signal energy into the higher coefficient vectors, leading to a sparse $W_4$ vector. This energy compaction leads to >99% of the total signal energy (% Energy) being packed into the $A_4$ coefficient vector across a sample of 253 unique EDA signals (Table 2, below). This allows the original signal to be compressed and reconstructed using very few wavelet coefficients, as shown in FIG. 7. The % Energy for each coefficient vector in Table 2 was computed for all 253 EDA signals and shows that a majority of signal energy in the wavelet domain can be retained with very few wavelet coefficients.

TABLE 2

Average percent energy of wavelet coefficient vectors.

| WT Vector | Mean % Energy | Std |
|---|---|---|
| $A_4$ | 99.98% | 0.04453% |
| $D_4$ | 0.01125% | 0.02632% |
| $D_3$ | 0.006232% | 0.01582% |
| $D_2$ | 0.002031% | 0.006512% |
| $D_1$ | 0.0008842% | 0.004310% |

Figure 18:
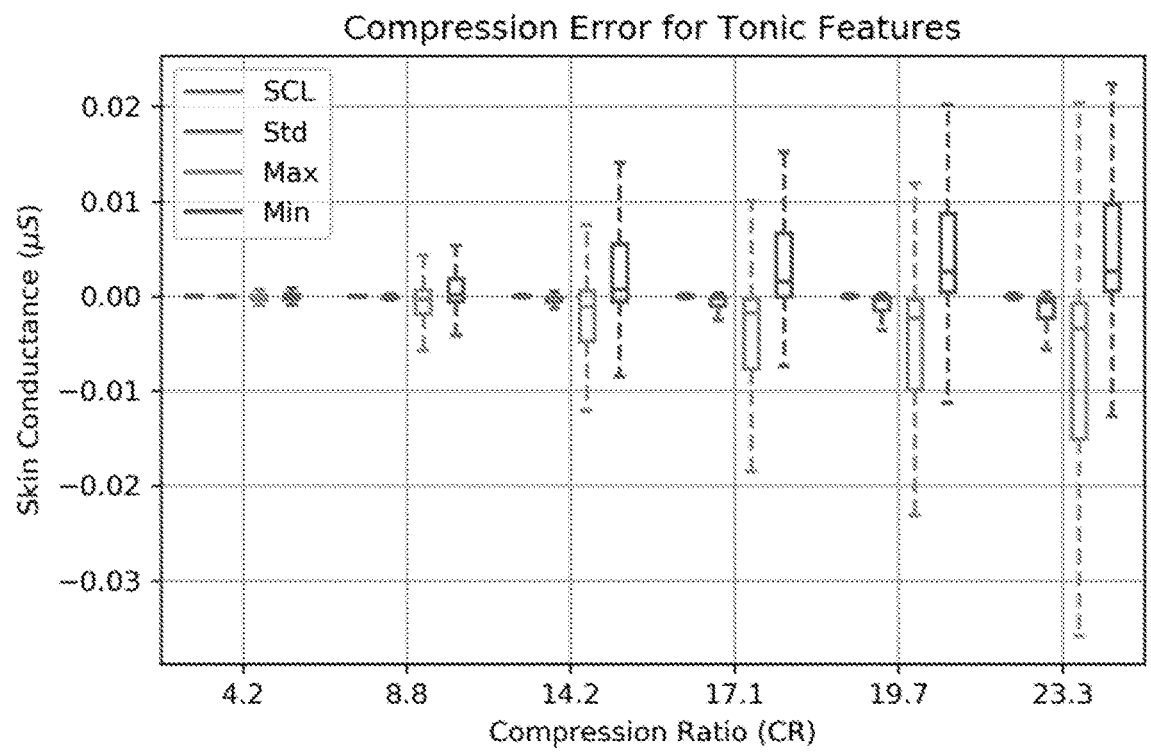
FIG. 18 plots absolute reconstruction errors of four electrodermal activity features, in an example.

The features of the EDA signal are not equally impacted at increasing compression ratios. As shown in FIG. 18, the tonic features are preserved quite well throughout the range of CRs. For each compression ratio, FIG. 18 shows the absolute reconstruction errors of four EDA features computed on 253 EDA signals that were collected during in-laboratory stress tests. For each compression ratio, FIG. 18 shows, from left to right, SCL (EDA mean), EDA standard deviation, EDA maximum, and EDA minimum. The SCL and standard deviation are hardly effected by compression. While the low-passing filtering effect of compressing the 1D array of wavelet coefficients introduces larger error on the EDA maximum and minimum at higher compression ratios, error within the interquartile remains below 0.015 µS for CRs up to CR=23.3×. SCL and standard deviation (Std) feature errors are <0.01 µS up to a CR of 23.3× and are negligible. Errors associated with the EDA maximum (Max) and minimum (Min) are effected more at higher compression ratios. The omission of detail coefficients at higher CRs has a low-pass filtering effect which moves the EDA signal Max and Min towards the mean SCL.

Figure 19:
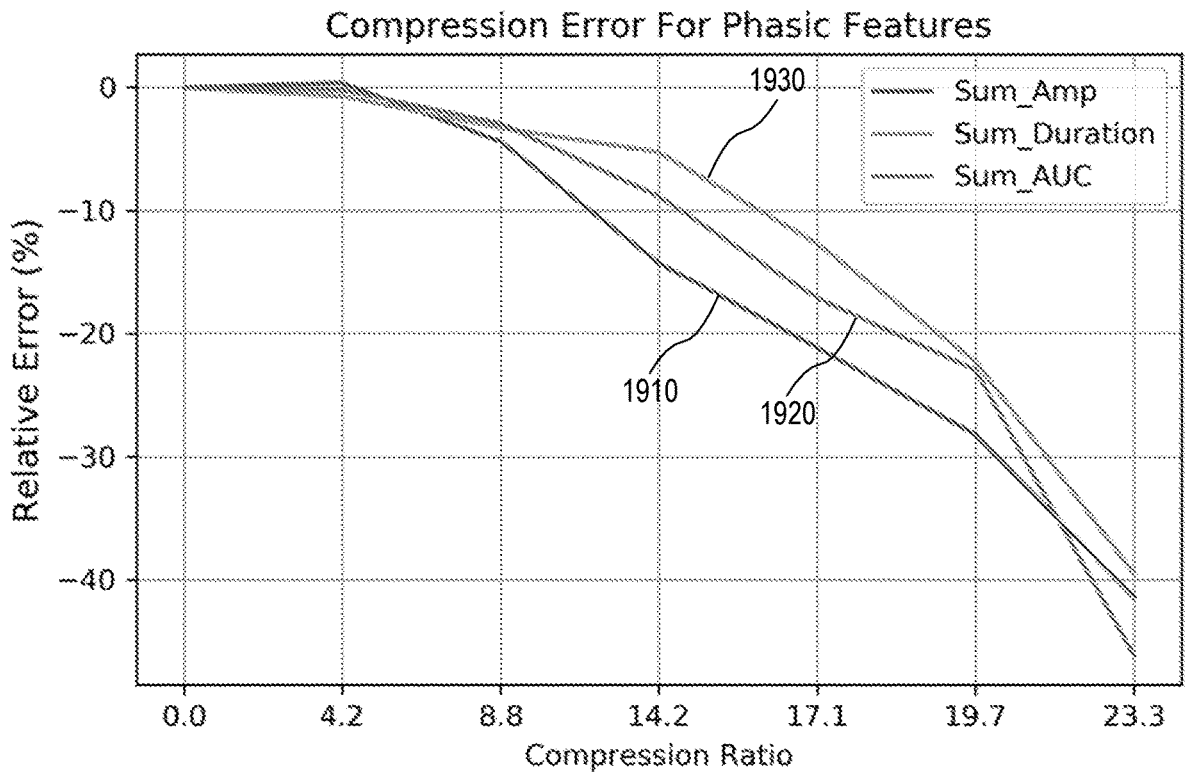
FIG. 19 plots relative error for the phasic electrodermal activity features, in an example.

Features related to phasic EDA (Sum_AUC, Sum_Amp, and Sum_Dur) are more sensitive to compression and experience greater errors at higher CRs, as shown in FIG. 19. FIG. 19 plots the relative error for the phasic EDA features-Sum of Area Under the Curve (labeled 1920), Sum of SCR amplitudes (labeled 1910), and the Sum Duration over 253 EDA signals (labeled 1930). Reconstruction errors are increased significantly above compression ratios of 8.8×, due to the loss of low-amplitude SCRs not being during the compression process. The relative errors for these features (based on the above expression for R(f)) show that the phasic features can be preserved quite well up to a CR of 8.8× with a relative error <5.0%. Above this CR, phasic feature errors increase, leading to a 28% relative error when CR=19.7×. Compression above this point begins to filter out SCRs of increasingly larger amplitudes—leading to relative errors exceeding 75% for the Sum_AUC, Sum_Amp, and Sum_Duration features as less information encoded within the detail coefficients is included in the compressed signal.

Figure 20:
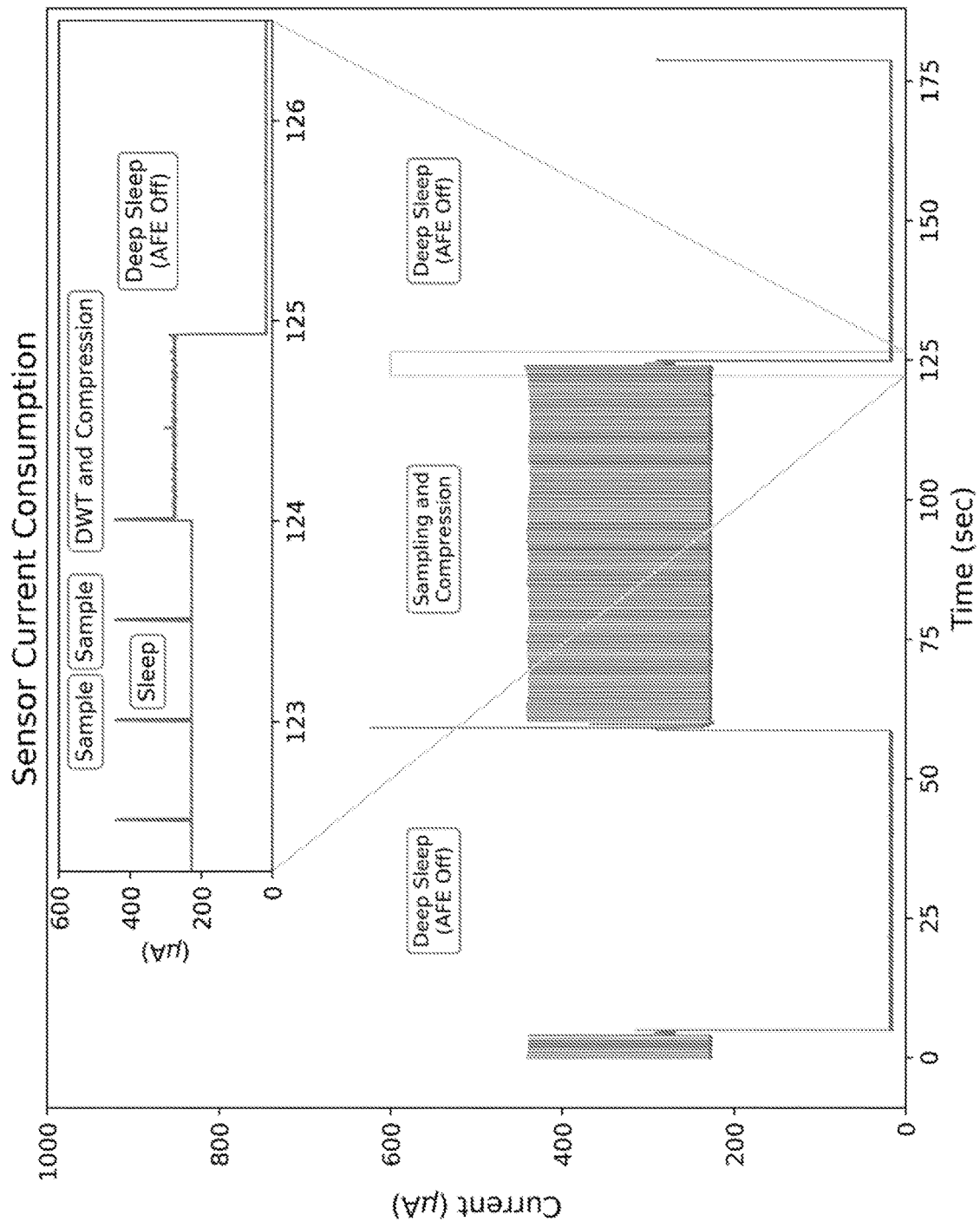
FIG. 20 shows current consumption of a microcontroller during its operation to record and store physiological data, according to an embodiment.

The designed system has high energy efficiency, consuming 655 µW for continuous EDA signal sampling, processing, and recording. FIG. 20 shows the current consumption between a 64 s sampling window (232 µA) and deep sleep modes (16.6 µA). These low power modes provide large energy savings when used in combination with periodic sampling method discussed previously. The average current draw is 16.6 µA during deep sleep mode, 232 µA for sampling the EDA signal, and 280 µA while processing the ML-DWT.

The processing of the ML-DWT, compression encoding, and data storage of the 128 sample EDA signal occurs within 0.92 s and requires an average current of 280 µA. This provides efficient end-to-end processing speed at low current consumption, making it competitive with traditional peripheral storage devices and wireless transmission methods used for data storage-especially given the relatively low clock rate of the MSP430 at 1 MHz.

Figure 21:
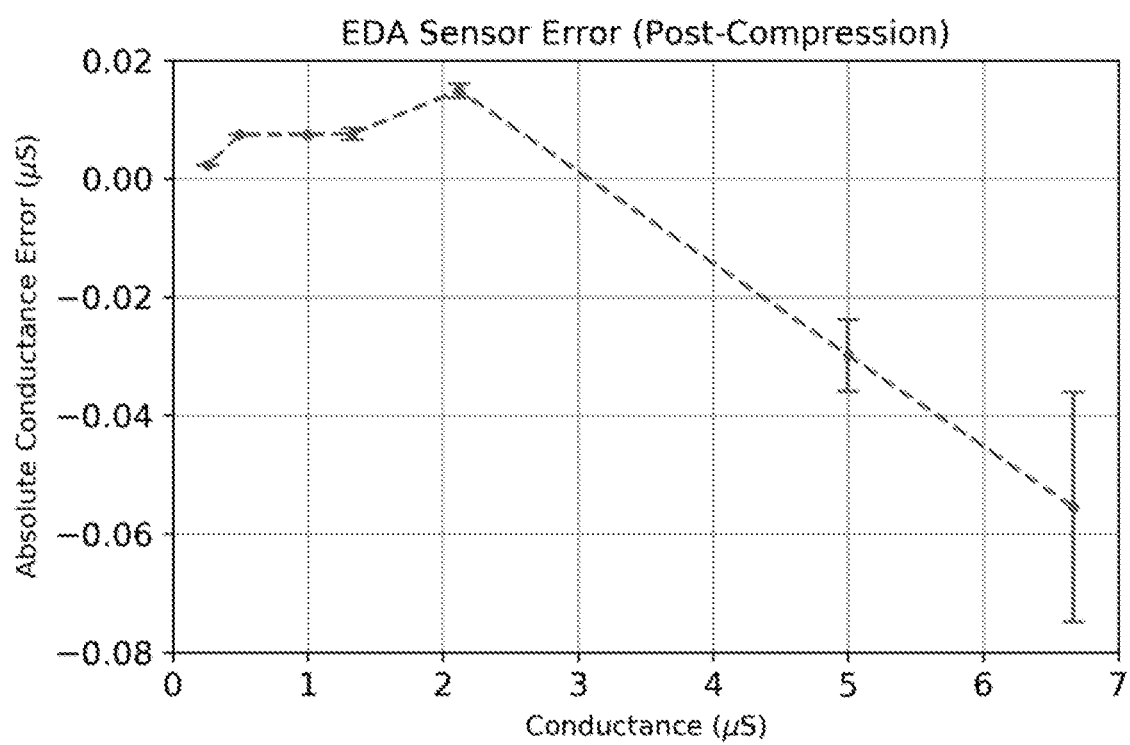
FIG. 21 plots the absolute error of an electrodermal activity sensor across a range of conductance values, in an example.

We evaluated the accuracy of the EDA sensor's analog front end on a range of fixed resistance values, as shown in FIG. 21. FIG. 21 plots the absolute error of the EDA sensor across a range of conductance values using the compression ratio (CR=17.1×). Each error measurement consists of 100 measurements of a known, fixed resistor having a conductance equal to G=1/R. The series of fixed resistors ranging 150 kΩ-3.88 MΩ were measured to determine the EDA sensor's conductance measurement error, using the formula G=1/R. FIG. 21 shows that the maximum conductance error is <0.075 iS for a range of conductance values between 0.25 µS-6.67 µS with a minimum sensitivity of 0.02 µS. Each error bar shown consists of 100 individual conductance measurements that were compressed on-board the MSP430 using a CR=17.1×.

This ultra-low resource sensor operates as a 'plug-and-play' recorder of electrodermal activity. Each sensor is designed to download data from the device to file on a laptop when the sensor is plugged in for charging. The charging cable also serves as a serial connection to the EDA sensor and a set of Python scripts are used to automatically download data from the device and configure it for the next recording. Each sensor can be programmed to record in 'Lab' mode which continuously records EDA without compression at a sample rate of 2 Hz or in 'Field' mode, in which EDA data is compressed before storing it into internal memory. Higher levels of compression lead to longer recording times at the expense of distorting EDA feature according to the results presented in FIGS. 18 and 19. Table 3, below, summarizes the maximum recording duration at a given compression ratio (CR) if saving data into the lower 48 KB of the MSP430FR5969.

TABLE 3

EDA recording duration for a given compression ratio (CR) using 48 kB of memory storage.

| Compression Ratio (CR) | Recording Duration (hours) |
| --- | --- |
| 0 | 0.60 |
| 4.20 | 2.52 |
| 8.80 | 5.28 |
| 14.20 | 8.52 |
| 17.10 | 10.26 |
| 19.70 | 11.82 |
| 23.30 | 13.98 |

Figure 22:
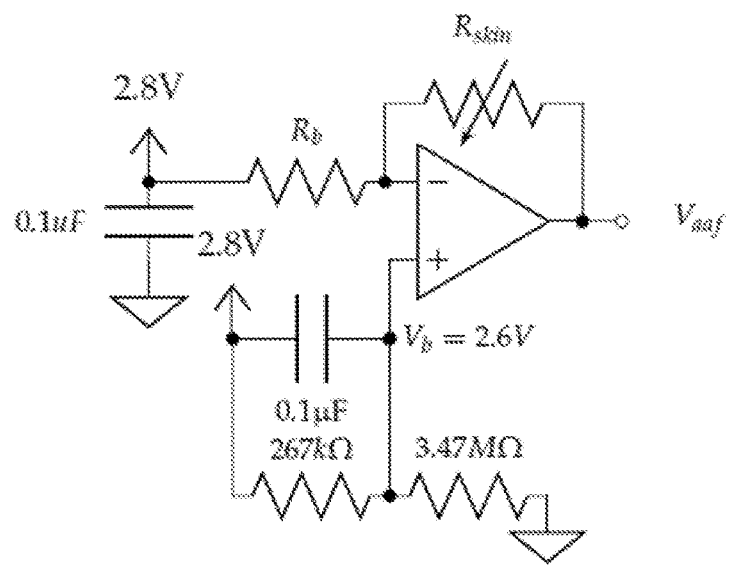
FIG. 22 is a circuit diagram for an electrodermal activity amplifier, according to an embodiment.

FIG. 22 shows the topology of EDA amplifier 1254. In this topology, the fixed voltage $V_b$ creates a 0.2 V voltage drop across resistor $R_b$=330 kΩ and establishes a quasi-constant current of 0.6 µA through resistor $R_{skin}$, the lumped resistance of the skin and contact electrodes. This topology was specifically designed to measure a fixed range of skin conductivities from 0.25 µS-6.67 µS (although a wider range from 0.01 µS-25 µS may be more appropriate for large populations).

A recent publication from Pabst et al. examines the nonlinear behavior of human skin when measuring skin impedance with low-frequency excitation voltages (0.2 V-1.2 V) and suggests that the EDA measurement itself may be affecting the underlying electrical properties of the skin during measurement when DC excitation voltages are >0.5 V (the standard method). Low-current measurements of EDA have been shown by Yamamoto and Yamamoto to reduce nonlinear affects and, more recently, Pabst et al. mention that further research into the nonlinear behavior of the skin at low current densities is still required. With an electrode area of 0.785 cm2, the developed system has a density of 0.6 µA/0.785 cm2=0.764 µA/cm2. The study from observes nonlinear electrical properties of the skin at higher excitation voltages and current levels. While the quasi-constant current circuit topology of EDA amplifier 1254 may have the benefit of maintaining low levels of current required for linear EDA measurement, it is understood that EDA 1254 may instead have an AC topology. AC topologies may provide additional benefits for linear operation at frequencies greater than 0.1 Hz. Alternatively, the topology of EDA amplifier 1254 could be modified to measure EDA using a constant-voltage model by exchanging the positions of $R_{skin}$ and $R_b$ and adjusting the reference voltage at $V_b$ such that the voltage drop across the skin is within a linear range of operation (0.2 V DC).

Figure 23:
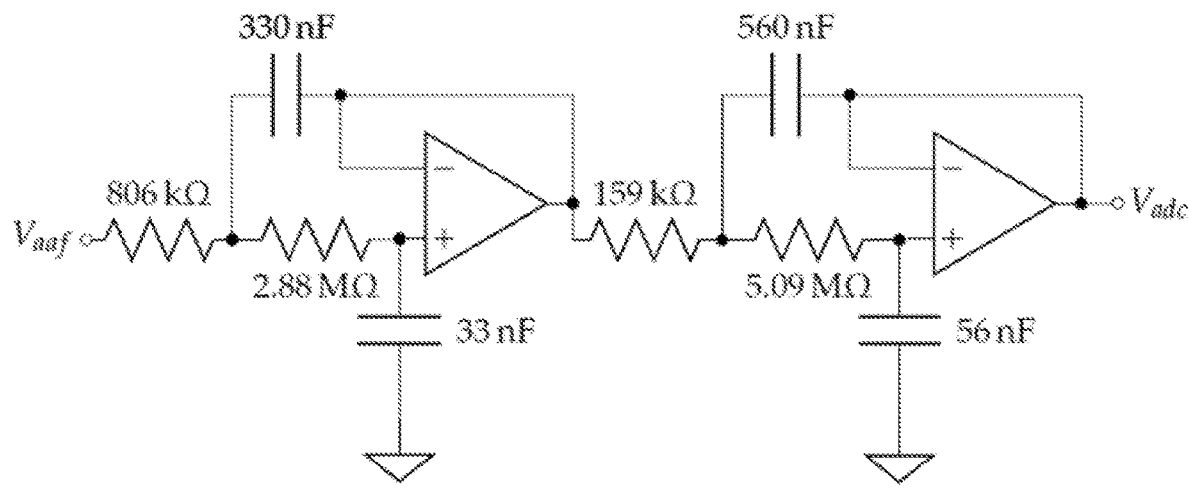
FIG. 23 is a circuit diagram for a low-pass filter, according to an embodiment.

FIG. 23 shows the topology of LPF 1256. Two Sallen-Key low-pass filters are cascaded to achieve a 4th order Butterworth filter with a 0 dB passband and a −3 dB cutoff frequency at 1 Hz.

Although Example 1 is concerned with EDA sensing, it is understood that the devices and methods used in Example 1 may be applied to sensing of other physiological signals, such as those discussed above in reference to FIGS. 1 and 2. The specific configurations used in Example 1 may be particularly suitable for recording and storing of aperiodic physiological signals having both tonic and phasic components.

Combinations of Features

Features described above as well as those claimed below may be combined in various ways without departing from the scope hereof. For example, it will be appreciated that aspects of one microcontroller for recording and storing physiological data, or associated device or method, described herein may incorporate or swap features of another microcontroller for recording and storing physiological data, or associated device or method, described herein. The following examples illustrate possible, non-limiting combinations of embodiments described above. It should be clear that many other changes and modifications may be made to the methods and device herein without departing from the spirit and scope of this invention:

(A1) One microcontroller for recording and storing physiological data includes an ADC for converting analog physiological sensor signals to digital signals, a sample buffer for holding a temporal sequence of the digital signals, a central processing unit (CPU), and a non-volatile memory. The non-volatile memory includes (i) a code storage encoding machine-readable data compression instructions that, when executed by the CPU, control the CPU to (a) transform the temporal sequence of the digital signals to produce transformed physiological data characterized by a set of transformation coefficients and (b) compress the set of transformation coefficients to generate compressed physiological data, and (ii) a data storage configured to contain several different instances of the compressed physiological data respectively associated with several different instances of the temporal sequence of the digital signals.

(A2) The microcontroller denoted as (A1) may be characterized by a current draw no greater than 10 milliamperes and a clock rate no greater than 32 megahertz, the non-volatile memory having capacity no greater than 1 megabyte, and the CPU being configured to process word lengths of no more than 24 bits.

(A3) In the microcontroller denoted as (A2), the current draw may be no greater than 0.1 milliamperes, the clock rate may be no greater than 16 megahertz, the non-volatile memory may have capacity no greater than 64 kilobytes, and the CPU may be configured to process word lengths of no more than 16 bits.

(A4) In any of the microcontrollers denoted as (A1) through (A3), the ADC may have a bit depth in range from 10 to 16 bits.

(A5) In any of the microcontrollers denoted as (A1) through (A4), the sample buffer may be a part of the non-volatile memory.

(A6) In any of the microcontrollers denoted as (A1) through (A5), the data compression instructions may be configured to (a) produce the set of transformation coefficients by applying a wavelet transformation to the temporal sequence of the digital signals, and (b) generate the compressed physiological data as a subset of the set of transformation coefficients.

(A7) In the microcontroller denoted as (A6), the wavelet transformation may be a multi-level wavelet transformation, wherein each level of the multi-level wavelet transformation produces a low-passed version and a band-passed version of an input signal to the level, and wherein the input signal to a first level includes the temporal sequence of the digital signals, and the input signal to each subsequent level is the low-passed version produced by the preceding level.

(A8) In the microcontroller denoted as (A7), the data compression instructions may include Daubechies scaling and wavelet coefficients.

(A9) In either of the microcontrollers denoted as (A7) and (A8), the low-passed version may be a wavelet approximation coefficients vector of the input signal, the band-passed version may be a detail coefficients vector, the set of transformation coefficients being a concatenation of the approximation coefficients vector of a last level and the detail coefficients vector of each level, and the compressed physiological data may consist of the approximation coefficients vector and the largest magnitude subset.

(A10) In the microcontroller denoted as (A9), the code storage may further include machine-readable data encoding instructions that, when executed by the CPU, control the CPU to encode the compressed physiological data in the data storage as (a) all values of the approximation coefficients vector, and (b) value and address, in the detail coefficients vector, of each of the detail coefficients of the largest magnitude subset.

(A11) In the microcontroller denoted as (A10), the data encoding instructions may be configured to encode (a) each entry of the approximation coefficients vector in a different respective word of the data storage, (b) each half of each address of at least a subset of the detail coefficients in a different respective word of the data storage also containing an entry of the approximation coefficients vector, and (c) each two values of the at least a subset of the detail coefficients together in a different respective word of the data storage.

(A12) In the microcontroller denoted as (A11), the non-volatile memory may have a word length of 16 bits, the ADC may have a bit depth of 12 bits, each entry of the approximation coefficients vector may have a word length of 12 bits, each entry of the detail coefficients vector may have a word length of 8 bits, and the temporal sequence of the digital signals may contain no more than $2^8$ digital signals.

(A13) In any of the microcontrollers denoted as (A7) through (A12), the machine-readable data compression instructions may be further configured to symmetrically pad the input signal to each level with M additional elements at each end of the temporal sequence of the pre-padding input signal, wherein M is a positive integer and the M additional elements at each end mirror M corresponding peripheral digital signals of the pre-padding input signal.

(A14) In any of the microcontrollers denoted as (A6) through (A13), the set of transformation coefficients may consist of N transformation coefficients and the most significant subset may be the K largest transformation coefficients, wherein N and K are positive integers and N/K>5.

(A15) In any of the microcontrollers denoted as (A1) through (A14), the data compression instructions may be interrupt-based.

(A16) One device for recording and storing physiological data includes a sensor for sensing a physiological parameter of a user and generating an analog physiological sensor signal representative of the physiological parameter, and any of the microcontrollers denoted as (A1) through (A15), further including, in the code storage, machine-readable sampling instructions that, when executed by the CPU, control the CPU to sample, via the ADC and at a sampling rate, the analog physiological sensor signals to generate the temporal sequence of digital signals.

(A17) The device denoted as (A16) may further include a frequency filter for filtering the analog physiological sensor signal prior to conversion by the ADC.

(A18) In the device denoted as (A17), the frequency filter may be a low-pass filter with a cutoff frequency no greater than one hertz.

(A19) In any of the devices denoted as (A16) through (A18), the sensor may be an electrodermal activity sensor.

(A20) In any of the devices denoted as (A16) through (A18), the sensor may be selected from the group consisting of a temperature sensor, a heart rate variability sensor, a surface electromyography sensor, an electroencephalography sensor, and a photoplethysmogram sensor.

(A21) In any of the devices denoted as (A16) through (A20), the sampling instructions may be interrupt-based.

(B1) One method for recording and storing physiological data may include, within a microcontroller, performing steps of (I) sampling, over time and via an analog-to-digital converter, an analog physiological sensor signal received by the microcontroller to produce a temporal sequence of digital signals, (II) transforming the temporal sequence of the digital signals to produce transformed physiological data characterized by a set of transformation coefficients, (III) compressing the set of transformation coefficients to generate compressed physiological data, and (IV) encoding the compressed physiological data in a non-volatile memory onboard the microcontroller.

(B2) In the method denoted as (B1), the analog physiological sensor signal may be aperiodic.

(B3) Either of the methods denoted as (B1) and (B2) may include repeating the steps of sampling, transforming, compressing, and encoding to store, in the non-volatile memory, a plurality of successive instances of the compressed physiological data.

(B4) Any of the methods denoted as (B1) through (B3) may include, in the step of transforming, applying a wavelet transformation to the temporal sequence of the digital signals to produce the set of transformation coefficients, and, in the step of compressing, generating the compressed physiological data as a subset of the set of transformation coefficients.

(B5) In the method denoted as (B4), the wavelet transformation may be a multi-level wavelet transformation and the step of transforming may include, for each level of the multi-level wavelet transformation, producing a low-passed version and a band-passed version of an input signal to the level, wherein the input signal to a first level includes the temporal sequence of the digital signals and the input signal to each subsequent level is the low-passed version produced by the preceding level.

(B6) In the method denoted as (B5), the low-passed version may be an approximation coefficients vector of the input signal, the band-passed version may be a detail coefficients vector, the set of transformation coefficients may be a concatenation of the approximation coefficients vector of a last level and the detail coefficients vector of each level, and the compressed physiological data may consist of the approximation coefficients vector and a largest-magnitude subset of the detail coefficients vector.

(B7) In the method denoted as (B6), the step of encoding may include encoding the compressed physiological data as (i) all values of the approximation coefficients vector, and (ii) value and address, in the detail coefficients vector, of each of the detail coefficients of the largest-magnitude subset.

(B8) In the method denoted as (B7), the step of encoding may include encoding (a) each entry of the approximation coefficients vector in a different respective word of the non-volatile memory, (b) each half of each address of at least a subset of the detail coefficients in a different respective word of the non-volatile memory also containing an entry of the approximation coefficients vector, and (c) each two values of the at least a subset of the detail coefficients together in a different respective word of the non-volatile memory.

(B9) In any of the methods denoted as (B5) through (B8), the step of transforming may further include symmetrically padding the input signal to each level with M additional elements at each end of the temporal sequence of the pre-padding input signal, wherein M is a positive integer and the M additional elements at each end mirror M corresponding peripheral digital signals of the pre-padding input signal.

(B10) In any of the methods denoted as (B4) through (B9), the set of transformation coefficients may consist of N transformation coefficients and the most significant subset may be the K largest transformation coefficients, wherein N and K are positive integers and N/K>5.

(B11) Any of the methods denoted as (B1) through (B10) may further include sensing a physiological parameter of a user to generate the analog physiological sensor signal as being representative of the physiological parameter.

(B12) The method denoted as (B11) may further include frequency filtering the analog physiological sensor signal prior to conversion by the analog-to-digital converter.

(B13) In the method denoted as (B12), the step of frequency filtering may include low-pass filtering the analog physiological sensor signal with a cutoff frequency no greater than 100 hertz.

(B14) In the method denoted as (B12), the step of frequency filtering may include low-pass filtering the analog physiological sensor signal with a cutoff frequency no greater than 1 hertz.

(B15) In any of the methods denoted as (B11) through (B14), the step of sensing may include sensing electrodermal activity.

(B16) In any of the methods denoted as (B11) through (B14), the step of sensing may include sensing a physiological property selected from the group consisting of respiration, heart rate variability, body temperature, brain activity, and muscle activity.

(B17) Any of the methods denoted as (B1) through (B16) may further include outputting the compressed physiological data to an external computer.

(B18) One method for obtaining physiological data includes performing the method denoted as (B17), and, onboard the external computer, at least approximately reconstructing the temporal sequence of digital signals from the compressed physiological data.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present systems and methods, which, as a matter of language, might be said to fall therebetween.

What is claimed is:

1. A microcontroller for recording and storing physiological data, comprising:
    an analog-to-digital converter (ADC) for converting analog physiological sensor signals to digital signals;
    a sample buffer for holding a temporal sequence of the digital signals;
    a central processing unit (CPU); and
    a non-volatile memory including:
    (i) a code storage encoding machine-readable data compression instructions that, when executed by the CPU, control the CPU to (a) transform the temporal sequence of the digital signals by applying a wavelet transformation to produce transformed physiological data characterized by a set of transformation coefficients, the set of transformation coefficients consisting of N transformation coefficients, the most significant subset being K largest transformation coefficients, N and K being positive integers, N/K>5, and (b) compress the set of transformation coefficients to generate compressed physiological data as a subset of the set of transformation coefficients, and
    (ii) a data storage configured to contain several different instances of the compressed physiological data respectively associated with several different instances of the temporal sequence of the digital signals.

2. The microcontroller of claim 1, characterized by a current draw no greater than 10 milliamperes and a clock rate no greater than 32 megahertz, the non-volatile memory having capacity no greater than 1 megabyte, the CPU being configured to process word lengths of no more than 24 bits.

3. The microcontroller of claim 2, the current draw being no greater than 0.1 milliamperes, the clock rate being no greater than 16 megahertz, the non-volatile memory having capacity no greater than 64 kilobytes, the CPU being configured to process word lengths of no more than 16 bits.

4. The microcontroller of claim 2, the ADC having a bit depth in range from 10 to 16 bits.

5. The microcontroller of claim 1, the wavelet transformation being a multi-level wavelet transformation, each level of the multi-level wavelet transformation producing a low-passed version and a band-passed version of an input signal to the level, the input signal to a first level including the temporal sequence of the digital signals, the input signal to each subsequent level being the low-passed version produced by the preceding level.

6. The microcontroller of claim 5, the data compression instructions including Daubechies scaling and wavelet coefficients.

7. The microcontroller of claim 5, the low-passed version being a wavelet approximation coefficients vector of the input signal, the band-passed version being a detail coefficients vector, the set of transformation coefficients being a concatenation of the approximation coefficients vector of a last level and the detail coefficients vector of each level, the compressed physiological data consisting of the approximation coefficients vector and the largest magnitude subset;
the code storage further including machine-readable data encoding instructions that, when executed by the CPU, control the CPU to encode the compressed physiological data in the data storage as (a) all values of the approximation coefficients vector, and (b) value and address, in the detail coefficients vector, of each of the detail coefficients of the largest magnitude subset;
the data encoding instructions being configured to encode (a) each entry of the approximation coefficients vector in a different respective word of the data storage, (b) each half of each address of at least a subset of the detail coefficients in a different respective word of the data storage also containing an entry of the approximation coefficients vector, and (c) each two values of the at least a subset of the detail coefficients together in a different respective word of the data storage; and
the non-volatile memory having a word length of 16 bits, the ADC having a bit depth of 12 bits, each entry of the approximation coefficients vector having a word length of 12 bits, each entry of the detail coefficients vector having a word length of 8 bits, the temporal sequence of the digital signals containing no more than $2^8$ digital signals.

8. A device for recording and storing physiological data, comprising:
a sensor for sensing a physiological parameter of a user and generating an analog physiological sensor signal representative of the physiological parameter; and
the microcontroller of claim 1, further including, in the code storage, machine-readable sampling instructions that, when executed by the CPU, control the CPU to sample, via the ADC and at a sampling rate, the analog physiological sensor signals to generate the temporal sequence of digital signals.

9. The device of claim 8, further comprising a frequency filter for filtering the analog physiological sensor signal prior to conversion by the ADC.

10. The device of claim 9, the frequency filter being a low-pass filter with a cutoff frequency no greater than one hertz.

11. The device of claim 8, the sensor being an electrodermal activity sensor.

12. The device of claim 8, each of the sampling instructions and the data compression instructions being interrupt-based.

13. A method for recording and storing physiological data, comprising, within a microcontroller, performing steps of:
sampling, over time and via an analog-to-digital converter, an analog physiological sensor signal received by the microcontroller to produce a temporal sequence of digital signals;
transforming the temporal sequence of the digital signals by applying a wavelet transformation to produce transformed physiological data characterized by a set of transformation coefficients, the set of transformation coefficients consisting of N transformation coefficients, the most significant subset being K largest transformation coefficients, N and K being positive integers, N/K>5;
compressing the set of transformation coefficients to generate compressed physiological data as a subset of the set of transformation coefficients; and
encoding the compressed physiological data in a non-volatile memory onboard the microcontroller.

14. The method of claim 13, the analog physiological sensor signal being aperiodic.

15. The method of claim 13, comprising repeating the steps of sampling, transforming, compressing, and encoding to store, in the non-volatile memory, a plurality of successive instances of the compressed physiological data.

16. The method of claim 13, the wavelet transformation being a multi-level wavelet transformation, the step of transforming comprising, for each level of the multi-level wavelet transformation, producing a low-passed version and a band-passed version of an input signal to the level, the input signal to a first level including the temporal sequence of the digital signals, the input signal to each subsequent level being the low-passed version produced by the preceding level;
the low-passed version being an approximation coefficients vector of the input signal, the band-passed version being a detail coefficients vector, the set of transformation coefficients being a concatenation of the approximation coefficients vector of a last level and the detail coefficients vector of each level, the compressed physiological data consisting of the approximation coefficients vector and a largest-magnitude subset of the detail coefficients vector;
the step of encoding comprising encoding the compressed physiological data as (i) all values of the approximation coefficients vector, and (ii) value and address, in the detail coefficients vector, of each of the detail coefficients of the largest-magnitude subset; and
the step of encoding comprising encoding (a) each entry of the approximation coefficients vector in a different respective word of the non-volatile memory, (b) each half of each address of at least a subset of the detail coefficients in a different respective word of the non-volatile memory also containing an entry of the approximation coefficients vector, and (c) each two values of the at least a subset of the detail coefficients together in a different respective word of the non-volatile memory.

17. The method of claim 16, the step of transforming further comprising symmetrically padding the input signal to each level with M additional elements at each end of the temporal sequence of the pre-padding input signal, M being a positive integer, the M additional elements at each end mirroring M corresponding peripheral digital signals of the pre-padding input signal.

18. The method of claim 13, further comprising sensing a physiological parameter of a user to generate the analog physiological sensor signal as being representative of the physiological parameter.

19. The method of claim 18, further comprising frequency filtering the analog physiological sensor signal prior to conversion by the analog-to-digital converter.

20. The method of claim 13, further comprising outputting the compressed physiological data to an external computer.

21. A method for obtaining physiological data comprising:
   performing the method of claim 20; and
   onboard the external computer, at least approximately reconstructing the temporal sequence of digital signals from the compressed physiological data.

* * * * *